(12) United States Patent
Paré et al.

(10) Patent No.: US 11,589,922 B2
(45) Date of Patent: Feb. 28, 2023

(54) MICROWAVE-ASSISTED MEDICAL TECHNOLOGIES AND APPARATUS THEREFOR

(71) Applicant: ATLANTIC CANCER RESEARCH INSTITUTE, Moncton (CA)

(72) Inventors: J. R. Jocelyn Paré, Moncton (CA); Jacqueline M. R. Bélanger, Moncton (CA)

(73) Assignee: Atlantic Cancer Research Institute, Moncton (CA)

( * ) Notice: Subject to any disclaimer, the term of this patent is extended or adjusted under 35 U.S.C. 154(b) by 0 days.

(21) Appl. No.: 17/372,063

(22) Filed: Jul. 9, 2021

(65) Prior Publication Data

US 2021/0386476 A1 Dec. 16, 2021

Related U.S. Application Data

(62) Division of application No. 16/088,262, filed as application No. PCT/CA2017/000077 on Apr. 5, 2017, now Pat. No. 11,090,115.

(30) Foreign Application Priority Data

Apr. 5, 2016 (CA) .................................. CA 2925827

(51) Int. Cl.
*A61B 18/18* (2006.01)
*A61B 18/06* (2006.01)
(Continued)

(52) U.S. Cl.
CPC .......... *A61B 18/1815* (2013.01); *A61B 18/06* (2013.01); *A61B 2018/00577* (2013.01);
(Continued)

(58) Field of Classification Search
CPC ................ A61B 18/1815; A61B 18/06; A61B 2018/00577; A61N 5/02
See application file for complete search history.

(56) References Cited

U.S. PATENT DOCUMENTS

| | | | |
|---|---|---|---|
| 5,002,784 A | 3/1991 | Paré et al. | |
| 5,338,557 A | 8/1994 | Paré | |

(Continued)

FOREIGN PATENT DOCUMENTS

| | | |
|---|---|---|
| CA | 2055390 | 5/1992 |
| CN | 1082569 C | 4/2002 |

(Continued)

OTHER PUBLICATIONS

Ahmed, M. et al., "Principles of and Advances in Percutaneous Ablation," Radiology, 258(2):351-369, (2011).

(Continued)

*Primary Examiner* — Thomas A Giuliani
*Assistant Examiner* — Christine A Dedoulis
(74) *Attorney, Agent, or Firm* — Alston & Bird LLP

(57) ABSTRACT

There is disclosed a method of treating affected external or surface tissue comprising the steps of providing a source of affected external or surface tissue; generating a source of microwave energy; transmitting said microwave energy into said affected external or surface tissues; exposing said affected external and surface tissues to said microwave energy to raise the local temperature to thereby ablate, remove, coagulate or otherwise alter said affected external and surface tissues. There is also disclosed an apparatus for the treatment of affected external and surface tissues comprising a microwave energy source generator, a means to transmit said microwave energy into said affected external or surface tissues, a means to control the exposure of said affected external and surface tissues to said microwave (Continued)

energy to raise the local temperature to thereby ablate, remove, coagulate or otherwise alter said affected external and surface tissues; and optionally a means to control the repetition of steps a) to d) multiple times until the ablation, removal, coagulation or otherwise alteration is complete, the period between each sequence of steps a) to d) being optionally cooled, and the location of said concentrated electric field being varied.

6 Claims, 12 Drawing Sheets

(51) Int. Cl.
A61B 18/00 (2006.01)
A61N 5/02 (2006.01)

(52) U.S. Cl.
CPC ............... A61B 2018/00589 (2013.01); A61B 2018/00601 (2013.01); A61B 2018/00994 (2013.01); A61N 5/02 (2013.01)

(56) References Cited

U.S. PATENT DOCUMENTS

| | | | |
|---|---|---|---|
| 5,377,426 A | 1/1995 | Paré | |
| 5,458,897 A | 10/1995 | Paré | |
| 5,519,947 A | 5/1996 | Paré | |
| 5,675,909 A | 10/1997 | Paré | |
| 5,732,476 A | 3/1998 | Paré | |
| 6,061,926 A | 5/2000 | Paré et al. | |
| 7,344,533 B2* | 3/2008 | Pearson | A61B 18/1477 606/41 |
| 8,343,095 B2 | 1/2013 | Cressman | |
| 8,444,635 B2 | 5/2013 | Lichtenstein et al. | |
| 9,498,284 B2 | 11/2016 | McErlean et al. | |
| 9,526,557 B2 | 12/2016 | Brannan | |
| 9,526,568 B2 | 12/2016 | Ohri et al. | |
| 9,526,576 B2 | 12/2016 | Brannan et al. | |
| 9,566,115 B2 | 2/2017 | van der Weide et al. | |
| 2002/0133139 A1* | 9/2002 | Moulis | A61M 25/10 604/523 |
| 2003/0073988 A1 | 4/2003 | Berube et al. | |
| 2006/0259024 A1* | 11/2006 | Turovskiy | A61B 18/1815 606/33 |
| 2012/0035608 A1 | 2/2012 | Marchitto et al. | |
| 2012/0310230 A1 | 12/2012 | Willis | |
| 2013/0289557 A1 | 10/2013 | Hancock et al. | |
| 2013/0324911 A1 | 12/2013 | Ohri et al. | |
| 2013/0345670 A1* | 12/2013 | Rajagopalan | A61B 18/04 604/506 |
| 2014/0088669 A1* | 3/2014 | Lanphere | A61P 9/10 607/96 |
| 2014/0276743 A1* | 9/2014 | Curley | A61B 18/1815 606/33 |
| 2014/0290830 A1* | 10/2014 | Brannan | A61B 18/1815 156/86 |
| 2015/0080875 A1 | 3/2015 | Kasprzyk et al. | |
| 2015/0272666 A1 | 10/2015 | Wang | |
| 2018/0110554 A1 | 4/2018 | Zarins et al. | |

FOREIGN PATENT DOCUMENTS

| | | |
|---|---|---|
| CN | 1453052 A | 11/2003 |
| CN | 201108822 Y | 9/2008 |
| CN | 104546126 | 4/2015 |
| JP | 3 095 241 | 10/2000 |
| JP | 2016-78183 A | 5/2016 |
| WO | WO 2013/157478 A1 | 10/2013 |
| WO | WO 2016/029022 A1 | 2/2016 |
| WO | WO 2017/173523 | 10/2017 |

OTHER PUBLICATIONS

Alfaro, M.J. et al., "Influence of solvent, matrix dielectric properties, and applied power on the liquid-phase microwave-assisted processes (MAP) extraction of ginger (*Zingiber officinale*)," Food Research International, 36:499-504, (2003).
Bélanger, J. et al., "4 Microwave-Assisted Processes in Food Analysis," Handbook of Food Analysis Instruments, Chapter 4, pp. 57-83, (2008).
Bélanger, J. et al., "Microwave-Assisted Extraction," Sample Preparation Handbook, Chapter 12, pp. 197-224, (2010).
Bélanger, J. et al., "Remarks on Various Applications of Microwave Energy," Journal of Microwave Power and Electromagnetic Energy, 42(4):24-44, (2007).
Brace, C. et al., "Microwave ablation technology: what every user should know," Curr. Probl. Diag. Radiol., 38(2):61-67, (2009).
Brace, C. et al., "Radiofrequency and microwave ablation of the liver, lung, kidney, and bone: what are the differences?," Curr. Probl. Diag. Radiol., 38(3):135-143, (2009).
Dou, J-P. et al., "Microwave ablation for liver tumors," Abdominal Radiology, 411:650-658, (2016).
Du, Q. et al., "Gelatin microcapsules for enhanced microwave tumor hyperthermia," Electronic Supplementary Material (ESI) for Nansoscale, The Royal Society of Chemistry, 11 pgs., (2015).
Goldberg, S.N. et al., "Radio-frequency thermal ablation with NaCl solution injection: effect of electrical conductivity on tissue heating and coagulation-phantom and porcine liver study," Radiology, 219(1):157-165, (2001).
Liu, Y. et al., "Optimization of microwave applicator for improved energy efficiency and homogeneity," chimica aggi/Chemistry Today, 29(4):14-17, (2011).
Mutyala, S. et al., "Design and Numerical Simulation of a High-efficiency Microwave Applicator for Industrial Processes," Hydrocarbon World, 6(1):71-75, (2011).
Mutyala, S. et al., "Microwave applications to oil sands and petroleum: A review," Fuel Processing Technology, 91:127-135, (2010).
Pare, J. et al., "Microwave-assisted process (MAP™) principles and applications," Techniques and Instrumentation in Analytical Chemistry, 18:395-420, (1997).
Pare, J. et al., "Microwave-assisted process (MAP™): a new tool for the analytical laboratory," Trends in Analytical Chemistry, 13:176-184, (1994).
Shi, H. et al., "Insights into a microwave susceptible agent for minimally invasive microwave tumor thermal therapy," Biomaterials, 44:91-102, (2015).
Yoon, J. et al., "High-frequency microwave ablation method for enhanced cancer treatment with minimized collateral damage," Int J. Cancer, 129:1970-1978, (2011).
AU Application No. 2617246249, Examination Report dated Apr. 5, 2019.
CA Application 3,017,029, Office Action dated Dec. 12, 2018.
CA Application 3,017,029, Office Action dated Oct. 9, 2018.
CA Application No. 3,017,029, Office Action dated Feb. 14, 2020.
CA Application No. 3,017,029, Office Action dated Mar. 18, 2019.
CA Application No. 3,017,029, Office Action dated Jul. 6, 2020.
CA Application No. 3,017,029, Office Action dated Oct. 22, 2019.
CN Application No. 201780017309.3, First Office Action dated Mar. 27, 2020.
CN Application No. 201780017309.3, First Search Report dated Mar. 7, 2020.
CN Application No. 201780017309.3, Second Office Action dated Sep. 29, 2020.
EP Application No. 17778496.4, Office Action dated Aug. 5, 2019.
EP Application No. 17778496.4, Office Action dated Dec. 5, 2019.
EP Application No. 17778496.4, Supplementary European Search Report dated Jun. 3, 2019.
EP Application No. 17778496.4, Supplementary Partial European Search Report dated Jan. 25, 2019.
IN Application No. 201817035490, Examination Report dated Jan. 25, 2021.
JP Application No. 2018-551286, Decision of Rejection dated Oct. 6, 2020.
JP Application No. 2018-551286, Office Action dated Feb. 4, 2020.

(56) References Cited

OTHER PUBLICATIONS

WIPO Application No. PCT/CA2017/000077, PCT International Search Report and Written Opion dated Aug. 1, 2017.

\* cited by examiner

MICROWAVE-ASSISTED MEDICAL TECHNOLOGIES AND APPARATUS THEREFOR

CROSS-REFERENCE TO RELATED APPLICATIONS

This application is a divisional of U.S. application Ser. No. 16/088,262, filed Sep. 25, 2018, which is a national phase entry of International Application No. PCT/CA2017/000077, filed Apr. 5, 2017, which claims priority to Canadian Patent Application No. 2,925,827, filed on Apr. 5, 2016, the entire contents of which are incorporated herein by reference.

FIELD OF THE INVENTION

The field of the invention relates to the control of microwaves through chemical means and the use of so controlled microwaves in medical, chemical, and plasma generation methods and apparatus to perform such methods.

BACKGROUND OF THE INVENTION

The use of microwave energy is spreading more widely in a large spectrum of activities. In fact several review papers have been published in a number of areas (Paré et al., 1994, 1997, 2003, 2008a, 2008b, 2010, 2011a, 2011b).

A relatively new area is that of microwave-based medical devices. Paré taught that it is possible to selectively heat one or more components of a material while leaving others relatively cool (U.S. Pat. Nos. 5,002,784; 5,338,557; 5,458,897). Paré also taught that it is possible to selectively heat one phase of a multi-phase system while leaving other phases relatively cool (U.S. Pat. Nos. 5,377,426; 5,519,947; 5,675,909; 5,732,476). These teachings on how to selectively destroy the microstructure of plant and animal tissues made these techniques most valuable for the extraction of a variety of high value-added compounds for example. Although most of these techniques were performed on ex situ tissues, they were shown to be applicable to in situ work. Hence there is a need to further make use of this selective heating characteristic of microwaves to develop methods and apparatus to be used in medical treatments.

There is also a need to further enhance such selective heating by using chemical means as opposed to physical means found in past teachings. Such chemical means to be used to modify the dielectric characteristics of the tissues so that said chemically treated tissues represent new materials to said microwave exposure and said chemically treated tissues are more susceptible to the microwave treatment.

Further, there is a need to provide for intelligent selective heating means that will be able to react proactively to the dielectric characteristics specific to the nature of the materials to be treated, whether said materials are tissues in their natural state or whether they have been subjected to the use of such chemical means thus providing for more precise treatment conditions and reduce or even remove the potential for damaging healthy tissues.

More specifically there is a need to harness the selective heating characteristics of microwaves to enhance the efficiency of chemical ablation procedures and broaden the range of their applicability in the medical field with some special emphasis in the area of oncology.

Still more specifically there is a need to harness the selective heating characteristics of microwaves to enhance the efficiency of chemical reactions procedures in general and broaden the range of their applicability in the chemical synthesis field with some special emphasis in the areas of liquid-phase synthesis and solid-phase synthesis, including high-temperature, fast pyrolysis. It will be evident to one skilled in the art that this invention applies equally well to other types of chemical reactions procedures and that the latter can be performed under pressure, under vacuum as well as under atmospheric pressure conditions.

More specifically there is a need to harness the selective heating characteristics of microwaves to enhance the efficiency of plasma generation procedures and broaden the range of their applicability in the chemical field with some special emphasis in the area of materials, nanotechnology, and electronics components. The deposition of carbon and diamond under plasma are representatives of such applications. It will be evident to one skilled in the art that this invention applies equally well to other types of procedures performed under plasma and that these two applications are provided only as typical examples and that they do not constitute an exhaustive list of applications nor are they limitative with respect to the extent of the applicability and the scope of this invention.

For the medical applications contemplated by this invention, the fundamental goal of the procedure lies in selectively heating affected tissues in vivo, whether in situ or ex situ, to a temperature and for a period of time sufficient to effectively ablate the affected tissues. It is possible to heat selectively affected tissues over healthy ones because, generally speaking, the former exhibit dielectric properties that are significantly different from those of the latter. Thus in principle it is relatively simple to effect such a procedure. But in actual cases, despite this general trend that affected tissues present dielectric properties favourable to heat selectively over healthy tissues, a universal procedure cannot be used because the dielectric properties of the various types of tissues vary significantly from one type of tissues to another one (e.g., liver versus lung).

Thus the challenge lies in being able to exercise a good control over the selective heating and to minimise the natural heat transfer that occurs between the heated affected tissues and the relatively cool healthy tissues so as to avoid damaging such healthy tissues and cause undue physiological stress to the patient.

It will be understood that this invention falls within the area of personalised medicine as each tissue to be treated will be in effect treated uniquely on a per patient basis and the exact treatment will be specific to a given tissue for a given patient and will vary between patients.

The blood that flows into or in the surroundings of the affected tissues can serve as a natural coolant. The relatively large mass of blood that flows into or in the surroundings of the affected tissues compared to the smaller mass of such affected tissues makes this a most suitable means to remove some heat and protect the healthy tissues against temperature increases.

It will be evident to those skilled in the art that there may be cases where the natural blood flow alone will not be sufficient to remove excess thermal energy and that it will be desirable to provide other means for effecting adequate cooling and prevent potential damages of the healthy tissues surrounding or near the affected tissues. Such means include, but are not limited to Peltier cooling, closed-loop liquid recirculation, gas expansion (e.g., $CO_2$), and the likes.

This additional cooling means will also have the enhanced benefit of cooling the components of the apparatus used to deliver such energy into affected tissues. This is especially important as thermal losses occur in for example a shaft such as a needle that in which is enclosed a means or a plurality of means to deliver the microwave energy, for example micro-coaxial cables, and that is used to guide the insertion and precise and judicious placement of such means to deliver microwave energy into the affected tissues.

Such thermal losses occur when the impedance of the device is not matched exactly during treatment. Even when the impedance is perfectly matched at the beginning of a treatment the impedance may drift during the treatment as the result of the evolution of the dielectric properties of the tissue as the necrotic process induced by the treatment proceeds and this gives rise to undesirable heat generation along the shaft of the apparatus.

It will also be evident to those skilled in the art that these perfect impedance matching conditions are not easily obtained and that the control over such conditions is critical. The challenge thus is to generate as a significant temperature gradient as possible while limiting the resulting thermal energy transfer to other physiological components.

The methods and devices used thus far are based upon power control and enhanced cooling. Paré et al. taught such methods to further enhance such selective heating by providing physical means to enhance the control of the energy density being applied to the system under treatment (U.S. Pat. No. 6,061,926). There are numerous such methods and apparatus. None of these are based on the dielectrics of the system. Dielectric parameters are the one Nature uses to differentiate between tissues; hence it is desirable to use such an approach.

It will be evident to those skilled in the microwave art that the electric field component of the microwave is a key parameter in the control of the energy transferred into a physiological system. There is a need to concentrate such electric field component into the tissues to be treated.

All techniques to date have made use of the pure power aspect of microwave energy. Some have used high-power devices. Some make use of an array of microwave-emitting antennas because the field between the antennas increases to the square of "n" when "n" antennas are used; this increase in field provides the potential to reach higher local temperatures. This approach however does not provide for any means to evacuate the thermal energy, nor does it preclude the electric field from being emitted toward the outside of the affected tissues as well as inside. To address the heat transfer problem, such apparatus also make use of additional cooling means; the latter makes them more complex and more cumbersome. There are no teachings to date on means to prevent excess field losses toward physiological components such as healthy tissues for example.

More recently, it has been proposed to use arched antennas (U.S. Pat. No. 8,808,282) and antennas coated with dielectric materials or with a face thereof masked to somewhat direct the electric field in a selected direction and limit its transmission in another (U.S. Pat. No. 6,692,492). However, none of these techniques addresses the variations in dielectrics between different types of tissue; say a bone tumour and a liver tumour. Hence there is a need to provide dielectric-based methods and apparatus to selectively and safely treat affected tissues, irrespective of the nature of the tissues.

There are no teachings to date on means to adapt in real time electrically to the evolving dielectric characteristics of the tissues under treatment be it by varying independently each probe used to emit the energy, whether the latter is via a mechanical movement of the probe, or by varying the electrical characteristics of the power being emitted. It will be evident to those skilled in the microwave ablation art that under such conditions the temperature increase that results from applying microwave energy to a tissue can be high enough to produce gases evolving and released by said tissues. These phenomena lead to reduced volume of the tissues being treated and by so doing augment significantly the risk of damaging surrounding non-diseased tissues that are getting closer to the application point of the microwave energy.

Further, it is known that such losses of materials lead to significant changes in dielectric properties, for example the dielectric constant. It will be evident to those skilled in the microwave art that such a reduction in dielectric constant gives rise to the potential for further penetration of the microwaves into the tissues and augments the risk of damaging surrounding non-diseased tissues. There are no teachings either on how to chemically control the evolution of the changes in dielectrics as the ablation procedure is performed. There are no teachings either on how to physically control the evolution of the changes in dielectrics as the ablation procedure is performed. There are no teachings on methods or devices to monitor and react in real time to such chemical and physical changes taking place during the necrosis process.

While liquids such as saline solutions have been introduced during microwave ablation treatments, they were used as a means to protect important physiological structures in the vicinity of the tissues to be treated (U.S. Pat. Nos. 8,343,095; 9,498,284; 9,526,557; 9,526,568; Goldberg et al. (2001); Du et al. (2015); Shi et al. (2015); Dou et al. (2016)). There are no teachings on using a susceptor such as a chemical ablation agent for the purpose of enhancing the efficiency of a chemical ablation treatment and to control the propagation of the electric field during the application of microwaves as an ablation treatment. Further, there are no teachings where such addition of a chemical ablation agent is performed through the energy transmitting means so as to not cause any perturbation of the electric field component of the microwave energy until the chemical ablation agent actually leaves the energy transmitting means.

More specifically there are no teachings on making use of the dielectric properties of substances used in chemical ablation procedures to combine the advantages of chemical ablation procedures and microwave ablation procedures to offer new procedures with enhanced efficiency and superior efficacy when compared to the performance of these procedures on their own. Such new microwave-assisted chemical ablation procedures are more universal as they apply to a broader range of tissues; they require less operation time to perform complete, non-invasive, ablation and provide for safer ablation procedures with respect to the potential of damaging surrounding non-diseased tissues. Further, there are no teachings on devices that can perform such procedures.

It will be evident to one skilled in the art that chemical ablation is one type of chemical reaction. It is fundamentally a pyrolysis oxidation reaction and it is governed by thermodynamic and kinetics principles similar to those of other chemical reactions. There are no teachings addressing these dielectric features in other types of chemical reactions.

It will also be evident to one skilled in the art that chemical reactions under microwaves can be carried in all phases of matter, namely, solid, liquid, gas, and plasma. There are no teachings addressing the judicious delivery of gaseous materials with the aim to generate larger and deeper plasma zones.

SUMMARY OF THE INVENTION

It will be evident to one skilled in the art that this invention applies equally well to ablation procedures as to coagulation procedures such as thermal coagulation necrosis, atrial fibrillation, resection, cautery, vascular thrombosis, treatment of cardiac arrhythmias and dysrhythmias, electro-surgery, tissue harvest, hemorrhoids thermal coagulation, and other types of thermal alterations. This list is provided only as a list of typical examples and is not exhaustive nor is it limitative with respect to the extent of the applicability and the scope of this invention.

It will also be evident to one skilled in the art that this invention applies equally well to other chemical reactions such as oxidative couplings, high-temperature pyrolysis, reductions, oxidations, and other types of chemical reactions performed in liquid-phase, solid-phase, or gaseous phase. This list is provided only as a list of typical examples and is not exhaustive nor is it limitative with respect to the extent of the applicability and the scope of this invention.

It will be further evident to one skilled in the art that this invention applies equally well to plasma generation procedures such as cold-discharge under microwaves, or the treatment of materials, nanotechnology, and electronics components including carbon or diamond deposition. This list is provided only as a list of typical examples and is not exhaustive nor is it limitative with respect to the extent of the applicability and the scope of this invention.

There is also a need to remove, ablate, or alter external tissues and surface tissues. This can vary from esthetic desire, such as the removal of warts, to more health-threatening congenital growths such as moles that can evolve into melanomas or provide a site for the development of melanomas.

Microwave technologies currently used in the medical field do not lend themselves to such applications. It will be evident to those skilled in the art that electric field losses from the current probes and antennas represent a safety threat to the practitioner if used outside the human body. Currently the human body practically acts as a shield because of the high dielectric constant of water that makes up a significant portion of the human tissues. Hence there are basically no electric field losses outside the body.

Thus to treat surface tissues or growths one must add an additional component to the apparatus to be used, namely a device capable to prevent electric field losses. The latter can be accomplished by providing an external shell to the antenna or probe, said shell made of a material that will absorb all electric field that can leak from said antenna or probe. It will be evident to those skilled in the art that such shell can be made as simply as providing an external jacket in which water is allowed to flow so as to not only absorb the electric field losses but also provide for a constant temperature procedure. It will also be evident to those skilled in the art that such device can be as complicated as to providing an electric means to effectively quench any electric field losses, as for example some form of Faraday cage or microwave choke.

The present invention, combined with the insertion of an additional component provides the means to apply it to surface and external tissues.

An important inventive step is the concentration of the electric field of the microwaves directly into the affected tissues. This can be achieved by various means. One such means consist in inserting simultaneously a second device that is coated or made of a material inert to physiological tissues and fluids and that has dielectric properties such that it will effectively serve as the electric load. Such a device can take various forms, a preferred one consisting of a needle-like probe which preferably has an antenna shape similar to that of the energy delivering antenna.

A most preferred means consists in delivering a dielectric material directly through the same device used to apply the microwave energy. In this case the material is preferably a liquid or is in solution. Such dielectric materials are generally called "susceptors".

It is thus evident that a judicious selection of the susceptor will make the method effective with any type of affected tissues and a truly universal method.

The susceptors to be used are selected for their ability to heat more rapidly and to higher temperatures while being subjected to microwave energy; thus reducing the power to be applied and remove the potential for field losses into other physiological components. Those skilled in the art will appreciate that faster heating also makes it possible to reduce the exposure time to the microwaves, thus further reducing the potential for field losses into other physiological components.

Further, the relatively small mass of the susceptor ensures that thermal losses to the healthy tissues, if any, will be insignificant while providing for a means to ensure efficient control over the thermal diffusion to said healthy physiological components, thus limiting damages and stress to the patient.

Such materials include, but are not limited to WC and the various forms of SiC. Such materials also include, but are not limited to, neat liquid materials and liquid solutions such as saline solutions and other substances having the desired dielectric and thermal properties. Such substances have the advantage of providing longer lasting stable impedance conditions by replacing the water being displaced by the heating process and thus provide for a faster means to heat selectively and to facilitate temperature elevation for a given level of energy being imparted while reducing or removing the thermal losses around the shaft of said energy transmitting means.

According to an embodiment of the present invention, there is provided a method of treating affected tissues comprising the steps of:
  a) providing a source of affected tissue;
  b) generating a source of microwave energy;
  c) transmitting said microwave energy into said affected tissue;
  d) delivering a susceptor into said affected tissue;
  e) concentrating the electric field component of said microwave energy in said affected tissue and said susceptor so as to increase selectively the temperature of said affected tissue and said susceptor;
  f) exposing said affected tissue and said susceptor to said concentrated electric field and increased temperature to thereby ablate, coagulate or otherwise thermally alter said affected tissues; and if desired;
  g) repeating steps a) to f) multiple times until the ablation, coagulation or the thermal alteration is complete.

According to another embodiment of the above method, steps a) to f) are repeated multiple times with a cooling period between each sequence until the ablation or coagulation is complete.

According to a further embodiment of the above method, the method utilizes at least one antenna with said antenna being capable of being retracted and introduced in a different location of tissue matter during the cooling step or between the repeating of steps b) to f).

According to a further embodiment of the above method, the susceptor in step d) is a drug to enhance the treatment efficiency or to reduce the post-treatment healing time.

Accordingly to a further embodiment of the above method, the affected tissue in step a) is surface or external tissue.

Desirably, the above method utilizes a cooling mechanism that is simultaneous to steps a) through f).

In a preferred embodiment a plurality of susceptor-coated antennas can be used to enhance the heating process without potential to have field losses that could harm other physiological components. It will be evident to those skilled in the art that penetration factor issues associated with 2450 MHz versus 915 MHz can be overcome without risk to other physiological components and that the use of 2450 MHz will be more ample than that offered by current technologies.

It will also be evident to those skilled in the art that these steps can be repeated a number of times in cases, for example where the affected tissue is tumoral and exhibits multiple nodules. In such cases one can repeat the steps without removing the device or devices allowing for thermal diffusion to a larger diameter around the probe or probes, or alternatively in removing it (them) and reinserting it (them) so as to reach a plurality of affected parts.

In another preferred embodiment of this invention a drug can also be used as the susceptor. Further, this invention can also be used to enhance the efficiency of drugs. The drug can be used to enhance the efficiency of the treatment, for example through toxicity towards the diseased tissues, or to improve the post-treatment process, for example through accelerated healing, or a combination thereof. It is well known that the temperature has a direct effect on the kinetics of a reaction as well as on the equilibrium of the reaction.

Hence there is a need to selectively heat a physiological entity such as affected tissues or fluids as a drug is being introduced into said physiological entity. Alternatively, there is a need to selectively heat a drug being introduced into said affected physiological entity. Further, alternatively, there is a need to selectively heat a drug being introduced into said affected physiological entity simultaneously as selectively heating said affected physiological entity.

It will be evident to those skilled in the art that the term drug is used to describe generally a substance or a combination of substances used to treat an ailment and that this drug can take various forms such as a pure liquid if it has the desired dielectric properties or a solution, a gel, or any combination thereof that exhibits the desired dielectric properties. This list is solely provided as a list of examples and is not exhaustive. It is not intended to limit the range of forms under which the drug can be introduced. The nature of the drug is also not limited by this general description.

This invention teaches a method to use microwave susceptor-coated devices to selectively heat a physiological entity at the point of introduction of a susceptor such as a drug.

Alternatively, this invention teaches a method to use microwave susceptor-coated devices to selectively heat a susceptor such as a drug as it is introduced and released within a physiological entity.

Further alternatively, this invention teaches a method to use microwave susceptor-coated devices to selectively heat a physiological entity at the point of introduction of a drug simultaneously to selectively heat a drug as it is introduced and released within a physiological entity.

It will be evident to those skilled in the art that this invention provides numerous advantages over current methods and apparatus such as smaller quantities because no metabolism occurs outside the local area surrounding the affected physiological entity. The reaction will exhibit a larger equilibrium constant due to the higher temperature at the reaction site in addition to lesser losses due to secondary reaction. The latter also offers the potential to reduce significantly side-effects due to products resulting from said secondary reactions. Side effects will also be reduced by the mere fact that lesser amounts of the drug or drugs will be used, thus reducing the stress on the physiological system and reducing the metabolic changes brought about by these foreign substances.

In the medical field the inventive steps and apparatus associated with this invention will benefit people suffering from a variety of diseases and ailments. It will contribute to improve their quality of life. It will find applications and use in the following areas:

Oncology
    Liver, lung, bone, endometrial, prostate, breasts, external tumours, etc.

Urology
    Benign prostate hypertrophy and prostate hypertrophy

Dermatology
    Removal of abnormal growth tissues, warts, etc.

Colorectal surgery or proctology
    Thermal coagulation of hemorrhoids

Cardiology
    Ablation of tissues (Cox-Maze procedure)
    Atrial fibrillation

Pharmacology
    Drug enhancement activity (for both in situ applications and for surface tissues)

This list is provided only as a list of typical examples and is not exhaustive nor is it limitative with respect to the extent of the applicability and the scope of this invention.

According to a further embodiment of the present invention, there is provided a method of treating affected tissue by enhancing the efficiency of a drug acting as a susceptor comprising the steps of:

a) providing a source of affected tissue;
b) generating a source of microwave energy;
c) transmitting said microwave energy into the affected tissue;
d) delivering a drug into said affected tissue while the temperature of said tissues is higher than normal and higher than surrounding tissue; and if desired
e) repeating steps b) through d) until the drug delivery is complete.

According to a further embodiment of the above method, steps a) to e) are repeated multiple times with a cooling period between each sequence until the drug delivery is complete.

According to yet a further embodiment of the above method, the method utilizes at least one antenna with said antenna being capable of being retracted and introduced in a different location of tissue matter during the cooling step or between the repeating of steps b) to d).

According to another embodiment of the above method, the method utilizes at least one antenna, with said antenna being capable of being retracted and introduced in a different location of tissue matter for the purpose of delivering said drug into said affected tissues during the cooling step or between the repeating of steps b) to d).

Desirably, there is provided a further embodiment of the above method wherein the method utilizes a cooling mechanism that is simultaneous to steps b) through d).

It will be evident to those skilled in the art that the word drug hereinabove contemplates a substance that can be composed of a single compound or a mixture thereof and that the word drug is used only as a typical example and that it does not constitute an exhaustive list of applications nor is it limitative with respect to the extent of the applicability and the scope of this invention.

According to a further embodiment of the present invention, there is provided a method of treating affected external or surface tissue by enhancing the efficiency of a drug acting as a susceptor comprising the steps of:
- a) providing a source of affected external or surface tissue;
- b) generating a source of microwave energy;
- c) transmitting said microwave energy into the affected external or surface tissue;
- d) providing a means to remove electric field losses to the surrounding non-tissue environment;
- e) delivering a drug into said affected external or surface tissue while the temperature of said tissue is higher than normal and higher than surrounding tissue; and if desired
- f) repeating steps b) through e) until the drug delivery is complete.

In a further embodiment of the above method steps a) to d) are repeated multiple times with a cooling period between each sequence until the drug delivery is complete.

According to another embodiment of the above method, the method utilizes at least one antenna, with said antenna being capable of being retracted and introduced in a different location of tissue matter during the cooling step or between the repeating of steps b) to e).

In a further embodiment of the above method, the method utilizes at least one antenna, with said antenna being capable of being retracted and introduced in a different location of tissue matter for the purpose of delivering said drug into said affected tissues during the cooling step or between the repeating of steps b) to e).

Desirably, in another embodiment of the method defined above, the method utilizes a cooling mechanism that is simultaneous to steps b) through e).

According to a further embodiment of the present invention, there is provided a method of treating affected tissue by enhancing the efficiency of a drug acting as a susceptor comprising the steps of:
- a) providing a source of affected tissue;
- b) generating a source of microwave energy;
- c) transmitting said microwave energy into the affected tissue;
- d) concentrating the electric field component of said microwave energy in the affected tissue so as to increase selectively the temperature of said affected tissue;
- e) delivering a drug into said affected tissue while the temperature of said tissue is higher than normal and higher than surrounding tissue; and if desired
- f) repeating steps b) through e) until the drug delivery is complete.

According to a further embodiment of the above method, steps b) to e) are repeated multiple times with a cooling period between each sequence until the drug delivery is complete.

According to yet another embodiment of the above method, the method utilizes at least one antenna with said antenna being capable of being retracted and introduced in a different location of tissue matter during the cooling step or between the repeating of steps b) to e).

According to a further embodiment of the above method, the method utilizes at least one antenna, with said antenna being capable of being retracted and introduced in a different location of tissue matter for the purpose of delivering said drug into said affected tissues during the cooling step or between the repeating of steps b) to e).

Desirably, there is provided the further embodiment wherein the method utilizes a cooling mechanism that is simultaneous to steps b) through e).

According to a further embodiment of the present invention, there is provided a method of treating affected external or surface tissue by enhancing the efficiency of a drug acting as a susceptor comprising the steps of:
- a) providing a source of affected external or surface tissue;
- b) generating a source of microwave energy;
- c) transmitting said microwave energy into the affected external or surface tissue;
- d) concentrating the electric field component of said microwave energy in the said affected external or surface tissue so as to increase selectively the temperature of said affected external or surface tissue;
- e) providing a means to remove electric field losses to the surrounding non-tissue environment;
- f) delivering a drug into said affected external or surface tissue while the temperature of said tissue is higher than normal and higher than surrounding tissue; and if desired
- g) repeating steps b) through f) until the drug delivery is complete.

According to another embodiment of the above method, steps b) to f) are repeated multiple times with a cooling period between each sequence until the drug delivery is complete.

According to yet another embodiment of the above method, the method utilizes at least one antenna, with said antenna being capable of being retracted and introduced in a different location of tissue matter during the cooling step or between the repeating of steps b) to f).

According to another embodiment of the above method, the method utilizes at least one antenna, with said antenna being capable of being retracted and introduced in a different location of tissue matter for the purpose of delivering said drug into said affected tissues during the cooling step or between the repeating of steps b) to f).

According to yet another embodiment of the above method, the method utilizes a cooling mechanism that is simultaneous to steps b) through f).

According to a further embodiment of the present invention, there is provided a method of treating affected tissue by enhancing the efficiency of a drug acting as a susceptor comprising the steps of:
- a) providing a source of affected tissue;
- b) generating a source of microwave energy;
- c) transmitting said microwave energy into a drug used to treat the affected tissue;
- d) delivering said drug into said affected tissue while the temperature of said drug is higher than room temperature and higher than surrounding tissue; and if desired
- e) repeating steps b) through d) until the drug delivery is complete.

In another embodiment of the above method, steps b) to d) are repeated multiple times with a cooling period between each sequence until the drug delivery is complete.

In yet another embodiment of the above method, the method utilizes at least one antenna, with said antenna being capable of being retracted and introduced in a different location of tissue matter during the cooling step or between the repeating of steps b) to d).

In a further embodiment of the above method, the method utilizes at least one antenna, with said antenna being capable of being retracted and introduced in a different location of tissue matter for the purpose of delivering said drug into said affected tissue during the cooling step or between the repeating of steps b) to d).

In a further embodiment of the above method, the method utilizes a cooling mechanism that is simultaneous to steps b) through d).

According to a further embodiment of the present invention, there is provided a method of treating affected external or surface tissue by enhancing the efficiency of a drug acting as a susceptor comprising the steps of:
 a) providing a source of affected external or surface tissue;
 b) generating a source of microwave energy;
 c) transmitting said microwave energy into the affected external or surface tissue;
 d) providing a means to remove electric field losses to the surrounding non-tissue environment;
 e) delivering a drug into said affected external or surface tissue while the temperature of said drug is higher than room temperature and higher than surrounding tissue; and if desired
 f) repeating steps b) through e) until the drug delivery is complete.

According to another embodiment of the above method, steps b) to e) are repeated multiple times with a cooling period between each sequence until the drug delivery is complete.

According to a further embodiment of the above method, the method utilizes at least one antenna, with said antenna being capable of being retracted and introduced in a different location of tissue matter during the cooling step or between the repeating of steps b) to e).

According to yet another embodiment of the above method, the method utilizes at least one antenna, with said antenna being capable of being retracted and introduced in a different location of tissue matter for the purpose of delivering said drug into said affected tissue during the cooling step or between the repeating of steps b) to e).

In a further embodiment of the above method, the method utilizes a cooling mechanism that is simultaneous to steps b) through e).

According to a further embodiment of the present invention, there is provided a method of treating affected tissues by enhancing the efficiency of a drug acting as a susceptor comprising the steps of:
 a) providing a source of affected tissue;
 b) generating a source of microwave energy;
 c) transmitting said microwave energy into a drug used to treat the affected tissue;
 d) concentrating the electric field component of said microwave energy in the drug used to treat affected tissue so as to increase selectively the temperature of said drug;
 e) delivering said drug into said affected tissue while the temperature of said drug is higher than room temperature and higher than surrounding tissue; and if desired
 f) repeating steps b) through e) until the drug delivery is complete.

According to an embodiment of the above method, steps a) to e) are repeated multiple times with a cooling period between each sequence until the drug delivery is complete.

According to yet another embodiment of the above method, the method utilizes at least one antenna, with said antenna being capable of being retracted and introduced in a different location of tissue matter during the cooling step or between the repeating of steps b) to e).

In a further embodiment of the above method, the method utilizes at least one antenna, with said antenna being capable of being retracted and introduced in a different location of tissue matter for the purpose of delivering said drug into said affected tissue during the cooling step or between the repeating of steps b) to e).

In yet a further embodiment of the above method, the method utilizes a cooling mechanism that is simultaneous to steps b) through e).

According to another embodiment of the present invention, there is provided a method of treating affected external or surface tissue by enhancing the efficiency of a drug acting as a susceptor comprising the steps of:
 a) providing a source of affected external or surface tissue;
 b) generating a source of microwave energy;
 c) transmitting said microwave energy into the affected external or surface tissue;
 d) concentrating the electric field component of said microwave energy in the drug used to treat affected external or surface tissue so as to increase selectively the temperature of said drug;
 e) providing a means to remove electric field losses to the surrounding non-tissue environment;
 f) delivering a drug into said affected external or surface tissue while the temperature of said drug is higher than room temperature and higher than surrounding tissues; and if desired
 g) repeating steps b) through f) until the drug delivery is complete.

According to a further embodiment of the above method, steps b) to e) are repeated multiple times with a cooling period between each sequence until the drug delivery is complete.

According to yet another embodiment of the above method, the method utilizes at least one antenna, with said antenna being capable of being retracted and introduced in a different location of tissue matter during the cooling step or between the repeating of steps b) to f).

According to yet another embodiment of the above method, the method utilizes at least one antenna, with said antenna being capable of being retracted and introduced in a different location of tissue matter for the purpose of delivering said drug into said affected tissue during the cooling step or between the repeating of steps b) to f).

According to a preferred embodiment of the above method, the method utilizes a cooling mechanism that is simultaneous to steps b) through f).

According to a preferred embodiment of the present invention, there is provided a method of treating affected tissues by enhancing the efficiency of a drug acting as a susceptor comprising the steps of:
 a) providing a source of affected tissue;
 b) generating a source of microwave energy;
 c) transmitting said microwave energy into a drug used to treat the affected tissue and into said affected tissue;
 d) delivering said drug into said affected tissue while the temperature of said drug and said affected tissue is higher than surrounding tissue; and if desired
 e) repeating steps b) through d) until the drug delivery is complete.

In a preferred embodiment of the above method, steps b) to c) are repeated multiple times with a cooling period between each sequence until the drug delivery is complete.

In another preferred embodiment of the above method, the method utilizes at least one antenna, with said antenna being capable of being retracted and introduced in a different location of tissue matter during the cooling step or between the repeating of steps b) to d).

In a further preferred embodiment of the above method, the method utilizes at least one antenna, with said antenna being capable of being retracted and introduced in a different location of tissue matter for the purpose of delivering said drug into said affected tissue during the cooling step or between the repeating of steps b) to d).

In another preferred embodiment of the above method, the method utilizes a cooling mechanism that is simultaneous to steps b) through d).

According to a preferred embodiment of the present invention, there is provided a method of treating affected external or surface tissue by enhancing the efficiency of a drug acting as a susceptor comprising the steps of:
 a) providing a source of affected external or surface tissue;
 b) generating a source of microwave energy;
 c) transmitting said microwave energy into a drug used to treat the affected external or surface tissue and into said affected external or surface tissue;
 d) providing a means to remove electric field losses to the surrounding non-tissue environment;
 e) delivering said drug into said affected external or surface tissues while the temperature of said drug and said affected external or surface tissue is higher than surrounding tissue; and if desired
 f) repeating steps a) through d) until the drug delivery is complete.

In a preferred embodiment of the above method, steps b) to e) are repeated multiple times with a cooling period between each sequence until the drug delivery is complete.

In another preferred embodiment of the above method, the method utilizes at least one antenna, with said antenna being capable of being retracted and introduced in a different location of tissue matter during the cooling step or between the repeating of steps b) to e).

In yet another preferred embodiment of the above method, the method utilizes at least one antenna, with said antenna being capable of being retracted and introduced in a different location of tissue matter for the purpose of delivering said drug into said affected tissue during the cooling step or between the repeating of steps b) to e).

In another preferred embodiment of the above method, the method utilizes a cooling mechanism that is simultaneous to steps b) through e).

According to a further preferred embodiment of the present invention, there is provided a method of treating affected tissue by enhancing the efficiency of a drug acting as a susceptor comprising the steps of:
 a) providing a source of affected tissue;
 b) generating a source of microwave energy;
 c) transmitting said microwave energy into a drug used to treat the affected tissue and into said affected tissue;
 d) concentrating the electric field component of said microwave energy simultaneously in the drug used to treat affected tissue so as to increase selectively the temperature of said drug and in the affected tissue so as to increase selectively the temperature of said affected tissue;
 e) delivering said drug into said affected tissue while the temperature of said drug and said affected tissue is higher than surrounding tissue; and if desired
 f) repeating steps b) through e) until the drug delivery is complete.

In a preferred embodiment of the above method, steps b) to e) are repeated multiple times with a cooling period between each sequence until the drug delivery is complete.

In another preferred embodiment of the above method, the method utilizes at least one antenna, with said antenna being capable of being retracted and introduced in a different location of tissue matter during the cooling step or between the repeating of steps b) to e).

In still another preferred embodiment of the above method, the method utilizes at least one antenna, with said antenna being capable of being retracted and introduced in a different location of tissue matter for the purpose of delivering said drug into said affected tissue during the cooling step or between the repeating of steps b) to e).

In a further preferred embodiment of the above method, the method utilizes a cooling mechanism that is simultaneous to steps b) through e).

There is also disclosed a method for enhancing the efficiency of a drug acting as a susceptor used for treatment of affected external or surface tissue, comprising the steps of:
 a) providing a source of affected external or surface tissue;
 b) generating a source of microwave energy and providing means to concentrate the electric field component of said microwave energy;
 c) providing a drug for treating said affected external or surface tissue;
 d) transmitting said microwave energy into said drug and into said affected external or surface tissue whereby the temperature of said drug is selectively increased and whereby the temperature of said affected external or surface tissue is also selectively increased;
 e) removing electric field losses to a surrounding non-tissue environment;
 f) delivering said drug into said affected external or surface tissues while the temperature of said drug and said affected external or surface tissues is higher than surrounding tissues.

Again, the method as described above, preferably comprises repeating steps b) through f) until drug delivery is completed.

The method as described above, desirably includes repeating the steps recited multiple times with a cooling period between each sequence until the drug delivery is complete.

Also, the method described above desirably utilizes at least one antenna capable of being retracted and introduced in a different location of tissue matter during the cooling step or between said repeating steps.

Further, the method described above, desirably utilizes at least one antenna being capable of being retracted and introduced in a different location of tissue matter for the purpose of delivering said drug into said affected tissues during the cooling step or between said repeating steps.

Further, the method described above utilizes a cooling mechanism that is simultaneous to said steps b) through f).

In a most preferred embodiment of the present invention as described earlier above, there is also disclosed a method for a microwave-assisted chemical ablation procedure used for treatment of affected tissues, comprising the steps of:
 a) providing a source of affected tissue;
 b) generating a source of microwave energy;
 c) transmitting said microwave energy into said affected tissue;
 d) delivering at least one chemical ablation substance into said affected tissue while transmitting said microwave energy into said affected tissue until the temperature of said chemical ablation substance and said affected tissue is higher than that of surrounding tissue; and if desired
 e) concentrating the electric field component of said microwave energy in the chemical ablation substance used so as to increase selectively the temperature of said substance and by so doing increase selectively and control the temperature of said affected tissue;

f) exposing said affected tissue to said concentrated electric field and said chemical ablation substance and said increased temperature to thereby ablate, coagulate or otherwise thermally alter said affected tissues; and if desired g) repeating steps b) to f) multiple times until the removal, ablation, coagulation or otherwise thermochemical alteration is complete.

In a further preferred embodiment of the above method, the means to transmit said microwave energy in step c) is also used to simultaneously deliver said chemical substance used for chemical ablation of step d).

In a preferred embodiment of the above method, steps b) to f) are repeated multiple times with a cooling period between each sequence until the removal, ablation, coagulation, or otherwise alteration is complete In another preferred embodiment of the above method, the method utilizes at least one antenna capable of being retracted and introduced in a different location of tissue matter during the cooling step or between the repeating of steps b) to f).

In still another preferred embodiment of the above method, the method utilizes at least one antenna capable of being retracted and introduced in a different location of tissue matter for the purpose of delivering said chemical ablation substance into said affected tissue during the cooling step or between the repeating of steps b) to f).

In a further preferred embodiment of the above method, the method utilizes a cooling mechanism that is simultaneous to steps b) through f).

It will be evident to those skilled in the art that a most preferred embodiment of the above method where a single means is used to simultaneously transmit said microwave energy and said chemical substance is when said chemical substance is delivered through a conduit that is within said microwave transmitting means. Preferably, said conduit is located at the very centre of said microwave transmitting means. One skilled in the art will appreciate that when said microwave transmitting means is composed of a metallic substance such a configuration respects Maxwell Equations in that said chemical substance is not exposed to said transmitted microwave energy until it leaves the endpoint of said microwave energy transmitting means. This makes for the optimal delivery of said microwave energy as said chemical substance does not interfere with said microwave energy delivery.

In a further preferred embodiment of the above method the delivery of said chemical ablation substance into said affected tissue while transmitting said microwave energy into said affected tissue of step d) if effected under such control so as to provide enough cooling capacity of said microwave energy transmitting means and thus remove the need for external cooling devices and materials.

In yet a further preferred embodiment of the above invention an additional step consisting of providing a means to remove electric field losses to the surrounding non-tissues environment is performed simultaneously to steps c) through f).

It will be evident to those skilled in the art that the basic teachings of this invention are very broad and will find utility in other fields. Ablation is fundamentally an oxidation reaction and is governed by thermodynamic and kinetics principles similar to those of chemical reactions. For example, it will be evident that the inventive step underlying the cases where a liquid such as ethanol is delivered via the same device that is used to transmit the microwave energy can be applied broadly to chemical synthesis under microwave irradiation.

There is also disclosed a method for a microwave-assisted chemical reaction procedure comprising the steps of:

a) providing a source of reaction medium consisting of at least one chemical reagent neat or in presence of a suitable solvent;

b) generating a source of microwave energy;

c) transmitting said microwave energy into said reaction medium until the temperature of said reaction medium is sufficient to effect the chemical reaction; and if desired d) delivering at least one other chemical reagent into said neat or solubilised chemical reagent while transmitting said microwave energy into new reaction medium until the temperature of said new reaction medium is sufficient to effect the chemical reaction;

e) concentrating the electric field component of said microwave energy into said chemical mixture so as to increase selectively the temperature of said reaction medium and by so doing increase selectively and control the temperature of said reaction medium; and f) maintain said microwave energy transmission until the chemical reaction or otherwise thermochemical alteration is complete.

In a preferred embodiment of the above method, steps b) to f) are repeated multiple times with a cooling period between each sequence until the reaction is complete.

In another preferred embodiment of the above method, the method utilizes at least one antenna, with said antenna being capable of being retracted and introduced in a different location of the reaction medium during the cooling step or between the repeating of steps b) to f).

In still another preferred embodiment of the above method, the method utilizes at least one antenna, with said antenna being capable of being retracted and introduced in a different location of the reaction medium for the purpose of delivering said chemical substance into said reaction medium during the cooling step or between the repeating of steps b) to f).

In a further preferred embodiment of the above method, the method utilizes a cooling mechanism that is simultaneous to steps b) through f).

In a further preferred embodiment of the above method, the means to transmit said microwave energy in step c) is also used to simultaneously deliver said chemical substance used for chemical reaction of step d).

It will be evident to those skilled in the art that a most preferred embodiment of the above method where a single means is used to simultaneously transmit said microwave energy and said chemical substance is when said chemical substance is delivered through a conduit that is within said microwave transmitting means.

In a further preferred embodiment of the above method the delivery of said chemical reaction substance into said reaction medium while transmitting said microwave energy into said reaction medium of step d) if effected under such control so as to provide enough cooling capacity and thus remove the need for external cooling devices and materials.

One skilled in the art will understand that under this preferred mode of operation the user can select chemicals or reagents offering a favourable combination of dielectric properties and solubility of the substances to be reacted, transformed or synthesized.

One skilled in the art will also recognise that the terms "solvent" and "solubilised" can be exchanged for "support" and "dispersed" as this invention also contemplates the performance of a solid-phase chemical reaction.

As per the ablation example, one skilled in the art will understand that selecting a substance with dielectric constant (permittivity) lesser than that of the customary medium or solvent used for a given chemical reaction will have for effect to concentrate the electric field by a factor of y/x where y is the permittivity of the customary solvent and x the dielectric constant of the added substance. This enhances the selectivity of the heating process within the reaction mixture. It brings about significant reduction in energy use and offers a better control on the temperature of the system. In fact one skilled in the art will recognize that a judicious selection of such a substance can allow for higher reaction temperatures and shorter reaction time, again as per the Arrhenius Equation. This is especially important when industrial-scale synthesis is concerned where the overall manufacturing costs is often governed by energy costs.

Further, it will be evident to those skilled in the art that reducing the reaction time brings about additional benefits such as reduced unwanted secondary reactions. This is especially true in cases where the kinetics of the side reactions is lesser than that of the desired reaction.

Still further, one skilled in the solid-state synthesis art will recognize that the use of this invention with a judicious selection of support and susceptor offers unparalleled economic advantages. For example, when selecting a suitable susceptor, like ethanol again, dispersed into solid support that absorbs microwaves along with chemical reagents devoid of good microwave absorption properties, will not only further increase the electric field into the support, thus allow for faster and higher reaction temperatures, which in turn lead to shorter reaction times, but offer the possibility in preferred cases contemplated by this invention to continue heating and remove the solvent in situ and thus lead to simplified recovery of the reaction products when compared to cases where one has to separate the reaction product from the reaction medium, e.g., by distillation or other separation means. Separation steps represent the bulk of processing costs for many syntheses, hence the use of this invention brings about significant economic advantages. One skilled in the art will appreciate that this is especially true for applications where the susceptor used is of relatively low boiling point, thus easy to remove by direct and simple microwave-assisted in situ distillation.

In the above narrative the word synthesis was used for conciseness and one skilled in the art will understand that it does not limit the applicability of the method to other treatments such as oxidative coupling, curing, sintering, flash evaporation, and other thermally sensitive reactions, transformations and processes. This list itself is also provided only as a list of typical examples and is not exhaustive nor is it limitative with respect to the extent of the applicability and the scope of this invention.

In another preferred embodiment of the above invention, there is also disclosed a method for a microwave-assisted chemical reaction procedure comprising the steps of:
a) providing a source of reaction medium consisting of at least one chemical reagents neat or in presence of a suitable solvent;
b) generating a source of microwave energy;
c) transmitting said microwave energy into said reaction medium until the temperature of said reaction medium is sufficient to effect the chemical reaction; and if desired
d) delivering at least one other chemical reagent into said neat or solubilised chemical reagent while transmitting said microwave energy into said neat or solubilised chemical reagent and into said additional chemical reagent or reagents until the temperature of said neat or solubilised chemical reagent and said additional chemical reagent or reagents is sufficient to effect the chemical reaction;
e) concentrating the electric field component of said microwave energy into said chemical mixture so as to increase selectively the temperature of said reaction medium and by so doing increase selectively and control the temperature of said reaction medium; and
f) maintain said microwave energy transmission until the chemical reaction or otherwise thermochemical alteration is complete.

It will be evident to those skilled in the art that the basic teachings of this invention are very broad and will find utility in still other fields. For example, it will be evident that the inventive step underlying the cases where a substance is delivered via the same device that is used to transmit the microwave energy can be performed using other substances such as gases.

In a preferred embodiment of this invention there is a method to use a gaseous substance and to deliver said substance through the same means of delivering the microwave energy into a reactor suitable to generate and maintain a plasma. The conditions for generating and maintaining said plasma will be well known to those skilled in the art. Those skilled in the art will also recognize that the delivery of said gaseous substance through the central shaft of the energy delivery mechanism brings about new means to generate plasma. It will also be evident to those skilled in the art that this invention allows for the use of a plurality of such antennas, each delivering said gaseous substance in order to create multi-point plasma generation, thus allowing unparalleled control on the plasma generation process and offers significant advantages in overcoming the limitations brought about by the dimension of the so-called skin sheath.

There is also disclosed a method for a microwave-assisted plasma generation procedure comprising the steps of:
a) providing a reaction chamber;
b) generating a source of microwave energy;
c) transmitting said microwave energy into said reaction chamber;
d) delivering at least one gaseous material into said reaction chamber through said microwave energy transmission means;
e) exposing said gaseous material to said microwave energy until said gaseous materials reached plasma conditions; and
f) maintain said exposure of said gaseous materials to said microwave energy until the desired process is complete.

In a preferred embodiment of the above method, the steps b) through f) are performed utilizing a plurality of equipment and devices.

Additionally, it will also be evident to those skilled in the art that for all these teachings, the energy delivery device or plurality of devices can be used and controlled independently and in real time to adapt to the evolving dielectric nature of the environment under treatment. For example, when a plurality of sources are used, each source can be used to measure the properties of the medium under treatment at the specific location where the energy delivery device is inserted and can react accordingly so as to maintain so-called adapted impedance conditions thus maximising the efficiency of the energy delivery process.

In a further preferred embodiment of the above method, the method utilizes a cooling mechanism to cool the microwave transmission means outside of the reaction chamber.

In a further preferred embodiment of the above method the delivery of said gaseous material into said reaction chamber while transmitting said microwave energy into said reaction chamber of step d) if effected under such control so as to provide enough cooling capacity and thus remove the need for external cooling devices and materials.

BRIEF DESCRIPTION OF THE FIGURES

These and certain other aspects of the present invention will now be described, by way of example only, with reference to the accompanying figures in which.

GENERAL ADVANTAGES/FEATURES

Figure 1:
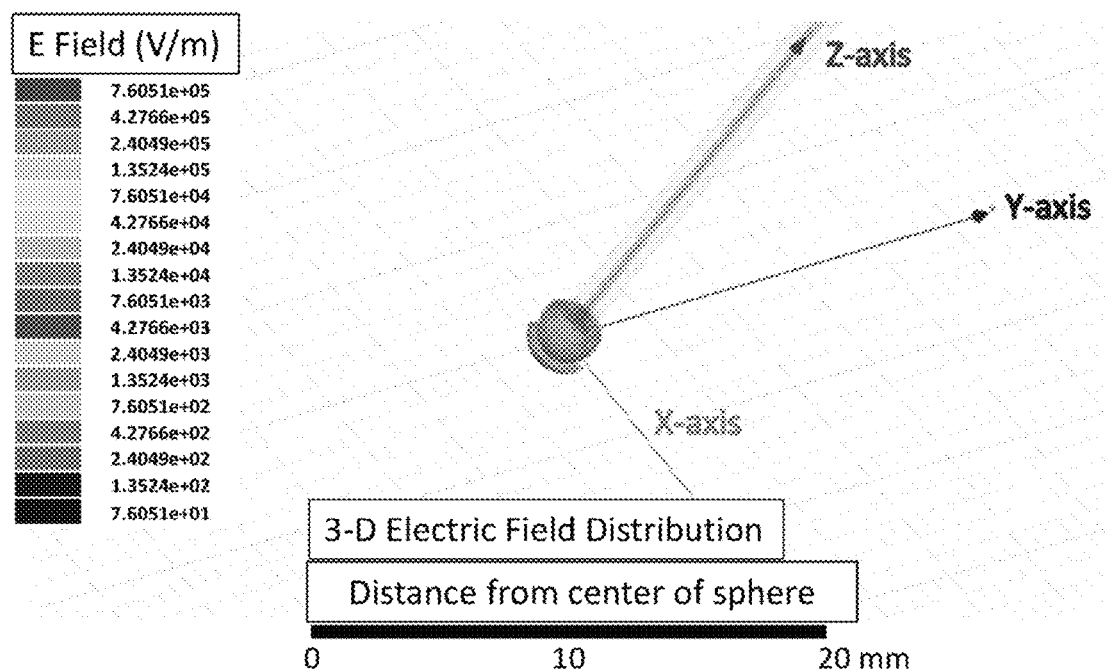
FIG. 1 shows the 3-dimensional electric field distribution along the conventional x-, y-, and z-coordinate axes when simulating a tumour ablation method performed under certain preferred embodiment conditions described in the present invention within a 3-mm diameter sphere with dielectric properties exhibited by a tissue wherein ethanol is used as a chemical ablation substance and is introduced through the central shaft of the microwave-emitting source directly into the center of the sphere.

One skilled in the art will appreciate all the innovative and most valuable utility benefits offered by the disclosed method for the treatment of tissues that combines the toxic effect of a chemical ablation substance to the thermal effect of microwaves in a procedure aiming to reach the necrosis stage of a tumour for example.

One skilled in the art will also recognise that the use of a chemical ablation substance, such as ethanol for example, a substance commonly used in the performance of a chemical ablation procedure, offers new and unparalleled advantages. For example, the ablation benefits from two mechanisms for treatment, namely the toxicity of ethanol and the heat produced by the microwaves.

Further, the toxicity of the ethanol is actually increased when compared to room temperature ethanol used in conventional chemical ablation procedures. Still further, the toxic effect of hot ethanol is faster than cool ethanol, thus leading to reduction in the time required to perform the ablative procedure.

Several physical characteristics of this invention also are without precedent and offer additional utility value to the use of the invention. For example at atmospheric pressure ethanol boils at 78 degrees C., a temperature exceeding largely the 41-43 degrees C. or so required to reach the necrosis stage of the affected tissues. Although this boiling point is increased when ethanol is introduced within cellular walls, it still allows maintaining a lower overall temperature for the tissues when compared to current procedures whereby the tissues are heated directly by the microwaves. This leads to reduced risk of collateral damages to healthy tissues due to thermal diffusion towards said healthy tissues. Tissues are composed mostly of water, and water boils above 100 degrees C. when contained within cellular walls. This results in a higher overall temperature of the tissues when only microwaves are used to heat the tissues directly. This leads to increased risks that thermal diffusion processes from affected tissues toward healthy tissues cause harm to healthy tissues.

Other benefits from physical parameters include the fact that ethanol has about half the heat capacity of water, thus ethanol has half the heat transfer capacity thus the risk of damaging healthy tissues is further reduced. Further, ethanol has a density considerably lower than that of water and body tissues thus again the risk of damaging healthy tissues is further reduced considerably as the energy transfer is based upon the mass, the heat capacity and the temperature of a substance.

In a preferred embodiment of this invention, the ethanol is delivered via the same device that is used to transmit the microwave energy. It will be evident to those skilled in the art that a most preferred embodiment of the above method where a single device is used to simultaneously transmit microwave energy and deliver the ethanol is when the ethanol is delivered through a conduit that is located in the centre of the microwave transmitting device. One skilled in the art will appreciate that when the microwave transmitting device is composed of a metallic substance then such a configuration respects Maxwell Equations in that the ethanol is not exposed to the transmitted microwave energy until it leaves the endpoint of the microwave energy transmitting device. This makes for the optimal microwave energy delivery as the ethanol does not interfere with the microwave energy delivery.

One skilled in the art will understand that under this preferred mode of operation the ethanol is heated only once it leaves the energy delivery antenna, by doing so it also can act as coolant for the antenna, thus removing the need for additional external cooling mechanisms used to protect healthy tissues between the point of entry into the body and the actual affected tissue location within the body. This reduces considerably the complexity, costs, and clutter of the apparatus design and simplifies the use thereof.

One skilled in the art will also understand that ethanol has a dielectric constant (permittivity) of about 10, while water has one of about 80, thus ethanol will concentrate the electric field by a factor of more than 8 into the ethanol that is in contact with affected tissues. This enhances the selectivity of the heating process within the affected tissues. This leads to much improved predictability of the shape and volume of the ablation zone. It further reduces the risk of damaging healthy tissues because the electric field penetration into surrounding healthy tissues that are devoid of ethanol is greatly hindered.

Finally, one skilled in the art will recognise that the unique combination of delivering the ethanol via the same device that is used to transmit the microwave energy and the evolution of the dielectric properties of the ethanol and that of the tissues leads to other desirable results. In some specific embodiments, this invention contemplates the delivery of the ethanol or other chemical substance used for the purpose of chemical ablation, via the central axis of the microwave-transmission device itself. For example, in such a configuration, during the ablation process the temperature of the surrounding tissues will elevate non uniformly effectively creating a gradient of temperature that will be relatively cool at the ethanol introduction point because of the continuous feeding of ethanol with the temperature increasing as one moves away from that point. This will be followed by a decrease in temperature after a certain distance from the introduction point as the penetration of the microwaves will be hindered by the ever increasing value of permittivity. This is a most desired effect. For example, as the temperature increases from about 35 to about 80 degrees C. the permittivity of the ethanol will vary from about 10 to basically 1 as it reaches its boiling point. Its loss factor on the other hand will not vary significantly while it is in liquid state as it will reduce from about 7.45 to 7.25. At the same time for those same variations in temperature the permittivity of water will vary from about 75 to about 60 and its loss factor from about 15 to about 2. One skilled in the art will appreciate that the occurrence of these variations in permittivity values simultaneously will have for effect to further reduce the field concentrating capacity of the ethanol as one moves away from the introduction point, thus again further protecting the healthy tissues from being harmed by the raise in temperature associated with the ablation procedure. Still further the occurrence of these variations in loss factor values simultaneously will have for effect to limit the extent of the thermal gradient from the energy emitting point and offer further protection to the healthy tissues against damages that can arise from the raise in temperature associated with the ablation procedure.

One skilled in the art will recognize that these phenomena can be easily visualized through the performance of some computer-aided simulation program. For example, FIGS. 1-7 herein provide the results obtained by performing a basic simulation of this invention using the commercially available HFSS software from Ansys. To show the extremely high utility value of this invention, the Applicant performed a one emitting-antenna modelling using very basic data set selected to represent the variation in electric field strength in function of distance within a spherical structure from the centre of the sphere—which is the delivery point of the ethanol for example—to the healthy tissues. One skilled in the art will recognize that this variation in electric field strength is directly related to the evolution of the dielectric properties of the tissue in function of the progression of the necrosis and the variations in temperature. To further highlight the extremely high utility value of this invention, the Applicant performed this modelling with no attempt to improve the performance through well-known techniques and electrical engineering strategies found in currently commercially available ablation tools such as slotted needles, ceramic or other dielectric materials at the end of the syringe, etc.

The model consisted of a set of 10 spheres of varying diameter (3, 5, 7, 9, 11, 13, 15, 17, 19, and 20 mm) characterized by varying dielectric properties (permittivity and loss factor), such values being chosen to be representative of the evolution of the continuous introduction of ethanol through the center of the microwave-emitting antenna as said ethanol gets diluted by the water contained into the tissues to be treated. The antenna was located at the very centre of the smaller sphere. The antenna outside diameter was 1.37 mm and was selected to be representative of a typical gauge 17 needle-type antenna currently in use in the field. The internal diameter allowing for the flow of ethanol was 0.42 mm. A nominal power of ca. 100 W was applied and the impedance adjusted to ca. 50 ohms.

Figure 2:
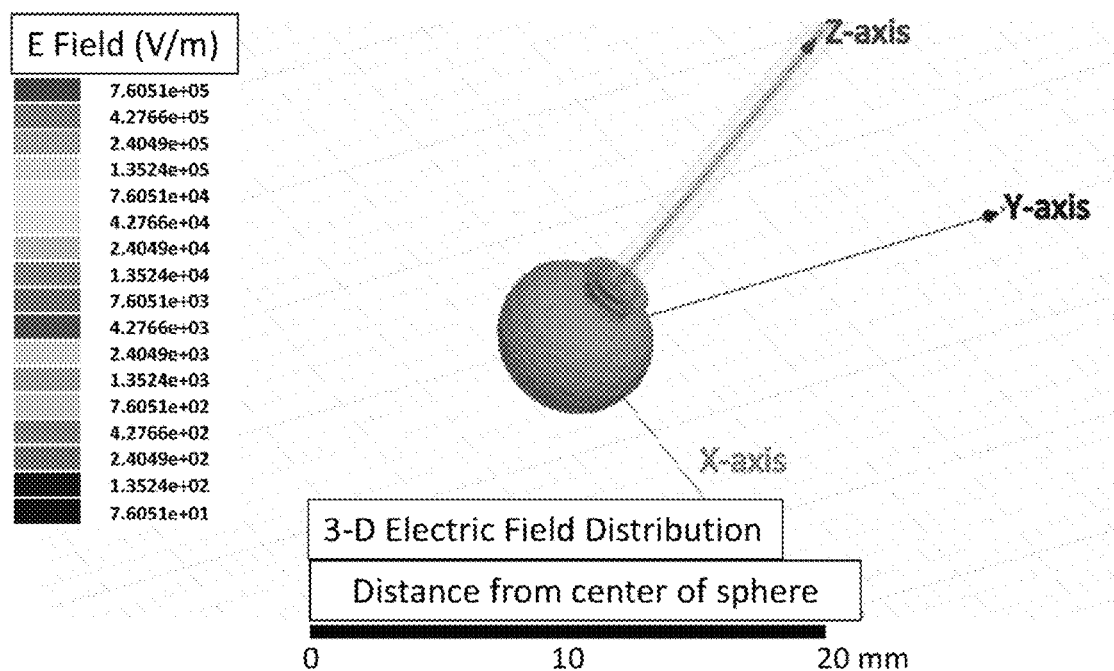
FIG. 2 shows the 3-dimensional electric field distribution along the conventional x-, y-, and z-coordinate axes when simulating a tumour ablation method performed under certain preferred embodiment conditions described in the present invention within a 9-mm diameter sphere with dielectric properties exhibited by a tissue wherein ethanol is used as a chemical ablation substance and is introduced through the central shaft of the microwave-emitting source directly into the center of the sphere.
Figure 3:
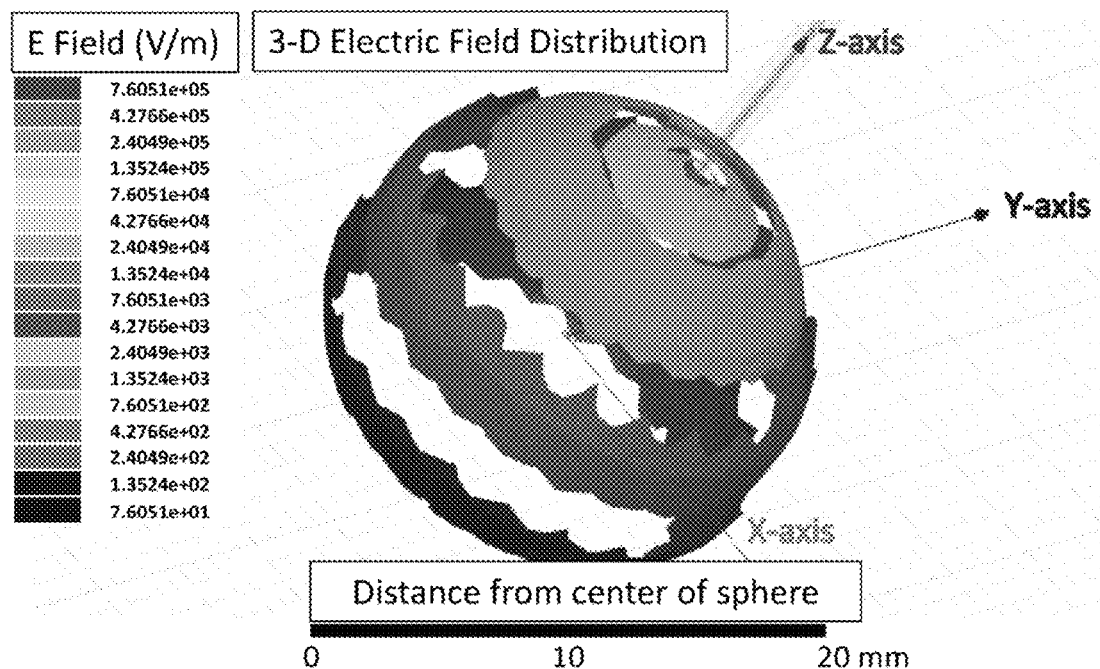
FIG. 3 shows the 3-dimensional electric field distribution along the conventional x-, y-, and z-coordinate axes when simulating a tumour ablation method performed under certain preferred embodiment conditions described in the present invention within a 20-mm diameter sphere with dielectric properties exhibited by a tissue wherein ethanol is used as a chemical ablation substance and is introduced through the central shaft of the microwave-emitting source directly into the center of the sphere.

The results clearly show the ability to achieve well-controlled nearly spherical heating of the tissues under treatment by using this invention. The latter being a most desirable feature of any ablation method. FIGS. 1 to 3 present data representative of the field configuration within the spherical volumes defined at 3, 7, and 20 mm, respectively, from the delivery point of the ethanol into the centre of the concentric spheres. Not only do the results show that near-spherical electric field distribution can be achieved but they show the well-defined gradient in the electric field strength a most desirable parameter to prevent collateral damages to neighbouring healthy tissues.

Figure 4:
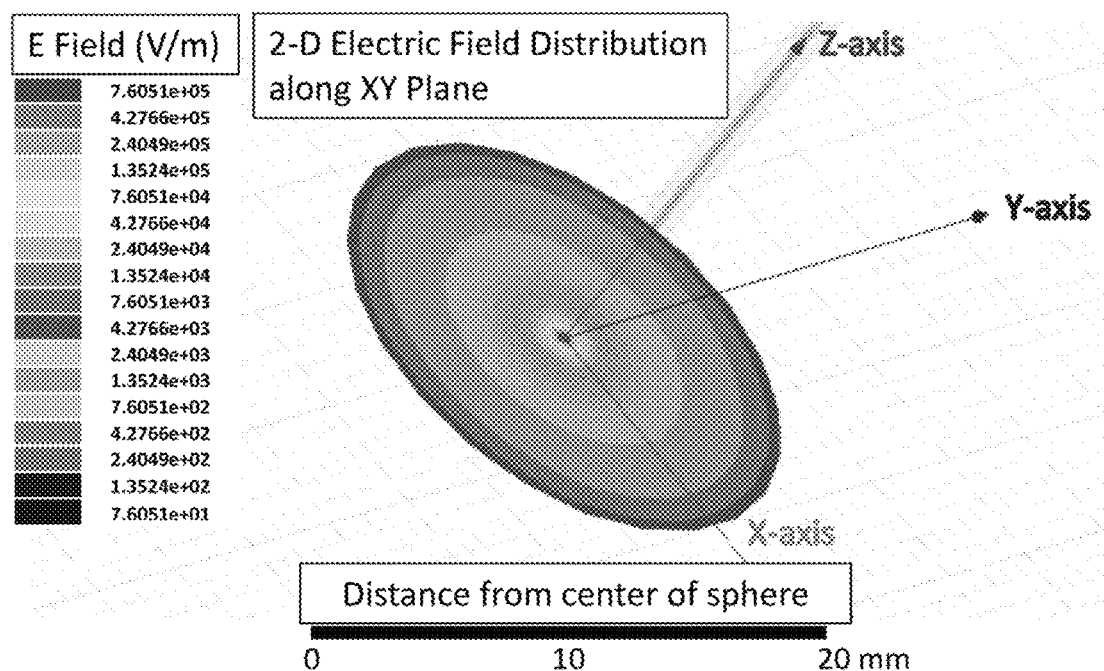
FIG. 4 shows the 2-dimensional electric field distribution along the conventional x- and y-coordinate axes (XY) plane when simulating a tumour ablation method performed under certain preferred embodiment conditions described in the present invention. The simulation was performed using dielectric properties values that vary as one moves away from the center of the simulated tumour and that are representative of those exhibited by a tissue being treated and wherein ethanol is used as a chemical ablation substance and is introduced through the central shaft of the microwave-emitting source directly into the center of the simulated tumour. A distance of 0 to 20 mm from the introduction point of the ethanol is shown therein.
Figure 5:
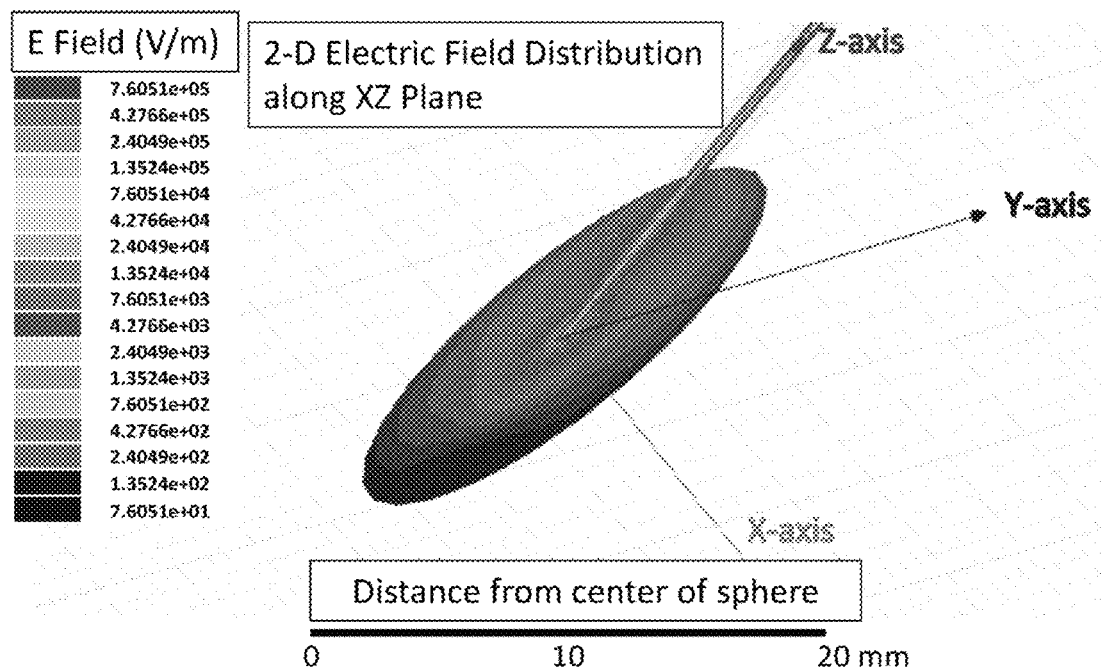
FIG. 5 shows the 2-dimensional electric field distribution along the conventional x- and z-coordinate axes (XZ plane) when simulating a tumour ablation method performed under certain preferred embodiment conditions described in the present invention. The simulation was performed using dielectric properties values that vary as one moves away from the center of the simulated tumour and that are representative of those exhibited by a tissue being treated and wherein ethanol is used as a chemical ablation substance and is introduced through the central shaft of the microwave-emitting source directly into the center of the simulated tumour. A distance of 0 to 20 mm from the introduction point of the ethanol is shown therein.

FIGS. 4 and 5 in turn show the electric field distribution along the XY and XZ planes, respectively. They provide ample evidence of the symmetrical pattern of the electric field.

Figure 6:
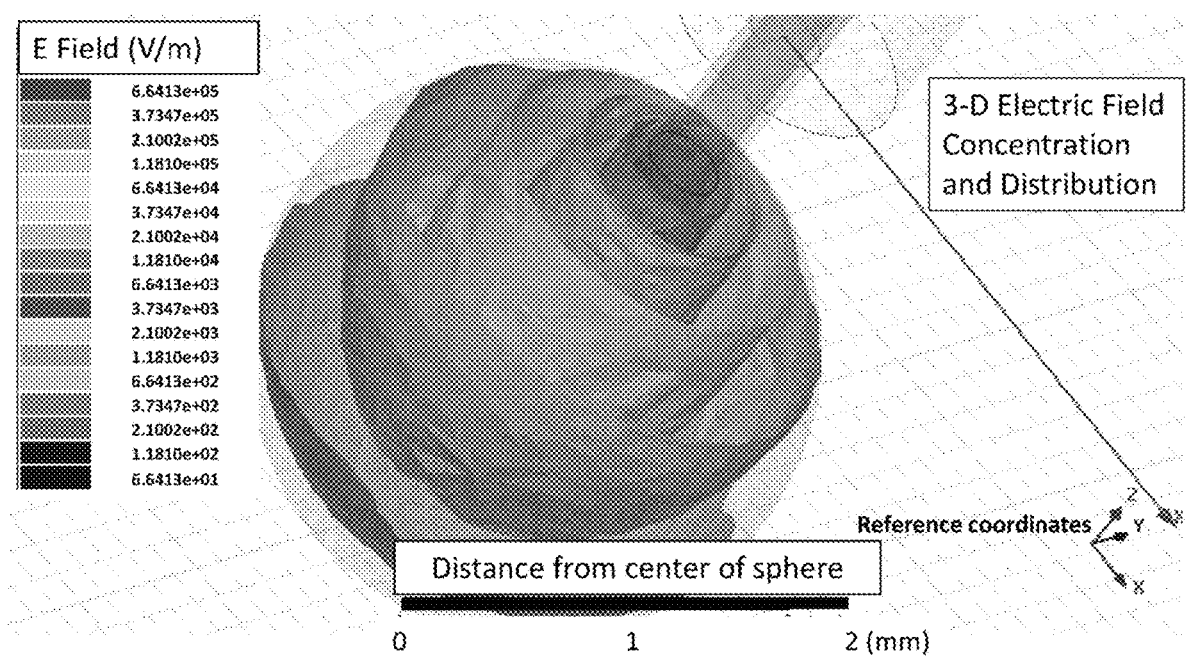
FIG. 6 shows the 3-dimensional electric field concentrating effect along the conventional x-, y-, and z-coordinate axes of using ethanol when simulating a tumour ablation method performed under certain preferred embodiment conditions described in the present invention. The simulation was performed using dielectric properties values that vary as one moves away from the center of the simulated tumour and that are representative of those exhibited by a tissue being treated and wherein ethanol is used as a chemical ablation substance and is introduced through the central shaft of the microwave-emitting source directly into the center of the simulated tumour. A distance of 0 to 2 mm from the introduction point of the ethanol is shown therein.
Figure 7:
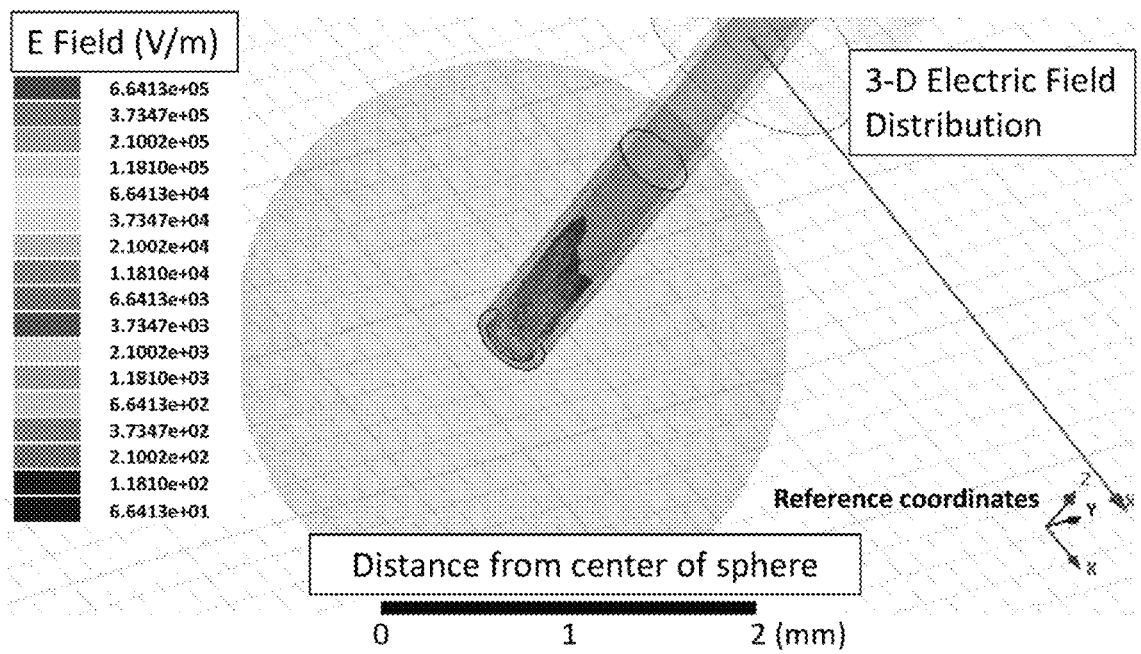
FIG. 7 shows that no undesirable effect is observed on the 3-dimensional electric field distribution along the conventional x-, y-, and z-coordinate axes such as energy loss or energy return into the microwave-emitting source occurs when simulating a tumour ablation method performed under certain preferred embodiment conditions described in the present invention wherein ethanol is used as a chemical ablation substance and is introduced through the central shaft of the microwave-emitting source directly into the center of the simulated tumour.

Further, FIGS. 6 and 7 show the clear benefit of delivering the chemical substance used for ablation—e.g., ethanol, through the central shaft of the microwave transmitting device and produce near-perfect spherical pattern. More specifically FIG. 6 explicitly demonstrates the capacity for the ethanol to concentrate the electric field. FIG. 7 in turn shows clearly that no undesirable effect is produced by this approach. Potential undesirable effects that were to be avoided included the potential for field and energy losses within the microwave-transmitting device. As seen in FIG. 7, the use of this invention is devoid from such drawbacks.

A small non-spherical behaviour can be noticed along the Z-axis, namely the axis where the microwave-transmitting device is introduced into the sphere (representing the tissue to be treated). One skilled in the art will recognize that this issue is easily explained by Maxwell's Equations and is the result of the fact that while the tip of the transmitting device is fixed by the microwave generating means, the potential along the outer portion of the microwave emitting means is not exactly at ground. The limiting conditions of Maxwell impose that the field be perpendicular to the conductor. Hence although the field emitted at the tip of the microwave emitting device adopts a spherical shape as it moves away from the tip, the presence of the conductor forming the external part of the microwave-emitting device modifies the polarization of the field toward the rear of the antenna.

One skilled in the art will know that this phenomenon can be mitigated and potentially removed by the introduction of at least one other microwave antenna judiciously located to provide similar field intensity variations in the other planes. The latter approach is contemplated by this invention and is a most preferred embodiment whenever the location and the nature of the tissue to be treated permit the use of such a multi-antenna method. Alternatively, it can also be mitigated by the introduction of short circuit in the microwave emitting means. The latter approach is also contemplated by this invention and is a most preferred embodiment whenever the location and the nature of the tissue to be treated do not permit the use of multi-antenna method.

To address this issue and further show the extremely high utility value of this invention, the Applicant performed a two emitting-antenna modelling using very basic data set selected to represent the variation in electric field strength in function of distance within a spherical structure from the centre of the sphere—which is the delivery point of the ethanol for example—to the healthy tissues. One skilled in the art will recognize that this variation in electric field strength is directly related to the evolution of the dielectric properties of the tissue in function of the progression of the necrosis and the variations in temperature. To further highlight the extremely high utility value of this invention, the Applicant performed this modelling with no attempt to improve the performance through well-known techniques and electrical engineering strategies found in currently commercially available ablation tools such as short-circuits, slotted needles, ceramic or other dielectric materials at the end of the antenna, etc.

All such configurations are being contemplated as suitable configurations by this invention, for example in one specific configuration the ethanol, or any other suitable susceptor, can be introduced through the central shaft of the microwave transmitting device and allowed to pearl outside the microwave energy delivery means through a suitable orifice such as, for example, a fritted tip made up of suitable dielectric material. The nature of the ethanol eluting tip is not limited by this general description.

The model consisted of a set of 10 spheres of varying diameter (3, 5, 7, 9, 11, 13, 15, 17, 19, and 20 mm) characterized by varying dielectric properties (permittivity and loss factor), such values being representative of the evolution of the continuous introduction of ethanol through the center of the microwave-emitting antenna as said ethanol gets diluted by the water contained into the tissues to be treated. Both antennas outside diameter was 1.37 mm, the latter being selected to be representative of a typical gauge 17 needle-type antenna currently in use in the field. Both internal diameters allowing for the flow of ethanol through each microwave-emitting antenna were 0.42 mm. A nominal power of ca. 100 W was applied at each antenna and the impedance adjusted to ca. 50 ohms for each antenna.

The antennas were introduced as follows: one antenna along the z-axis down to 2 mm from the centre of the smaller sphere; the second antenna in the same plane but at an angle of 135 degrees with respect the z-axis and also at 2 mm from the centre of the smaller sphere. A simulation was performed while maintaining the antennas in-phase with each other and another simulation was performed with a phase-shift of 90 degrees between the antennas.

Figure 8:
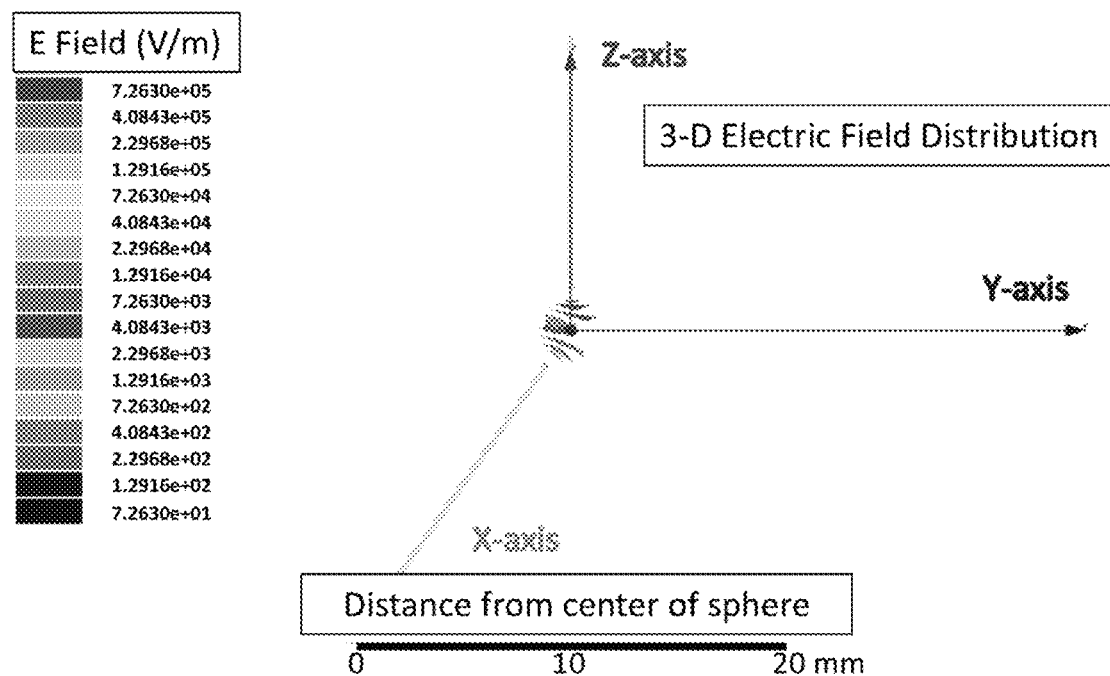
FIG. 8 shows the electric field distribution along the conventional x-, y-, and z-coordinate axes when simulating a tumour ablation method performed using two distinct and independent microwave-emitting sources located at 135 degrees from each other under certain preferred embodiment conditions described in the present invention within a 3-mm diameter sphere with dielectric properties exhibited by a tissue wherein ethanol is used as a chemical ablation substance and is introduced through the central shaft of the microwave-emitting sources near the center of the sphere. The two microwave-emitting sources used were of the same phase.
Figure 9:
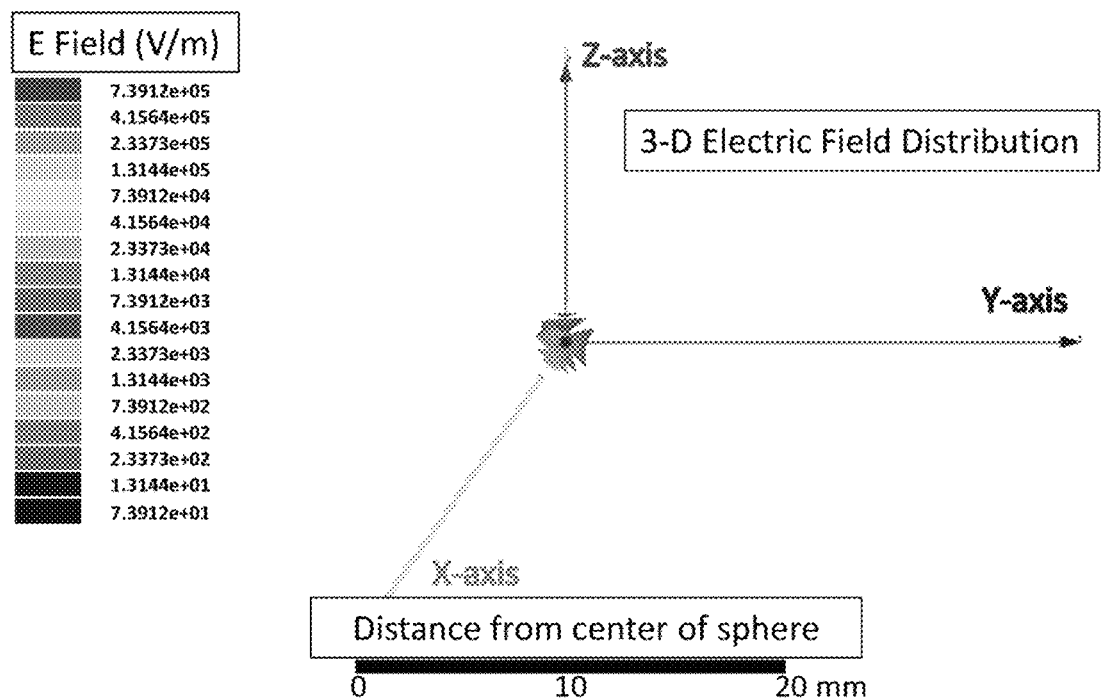
FIG. 9 shows the 3-dimensional electric field distribution along the conventional x-, y-, and z-coordinate axes when simulating a tumour ablation method performed using two distinct and independent microwave-emitting sources located at 135 degrees from each other under certain preferred embodiment conditions described in the present invention within a 3-mm diameter sphere with dielectric properties exhibited by a tissue wherein ethanol is used as a chemical ablation substance and is introduced through the central shaft of the microwave-emitting sources near the center of the sphere. The two microwave-emitting sources used were phase-shifted by 90 degrees.
Figure 10:
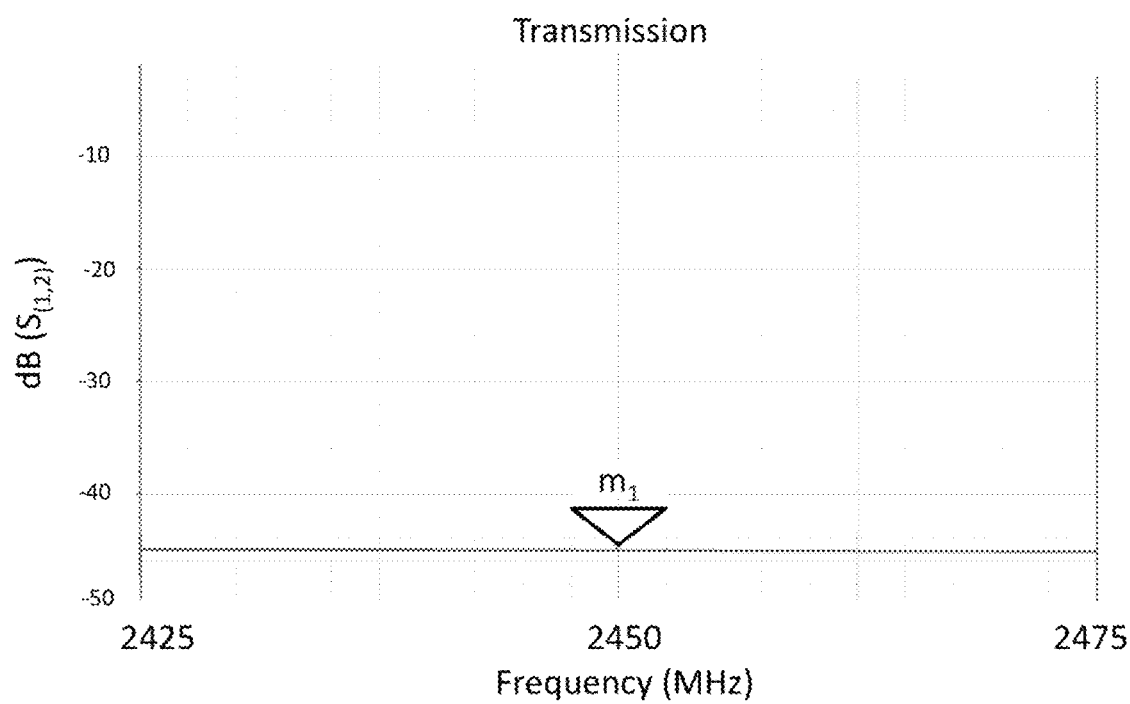
FIG. 10 presents the $S_{1,2}$ results for the 90 degrees phase-shifted experiment presented in FIG. 9.

FIGS. 8-10 herein provide the results obtained by performing such basic simulations. FIGS. 8 and 9 show the experimental setup for the in-phase and the 90 degrees phase-shifted experiments, respectively.

FIG. 10 presents the $S_{1,2}$ results for the 90 degrees phase-shifted experiment. The latter (−45 dB) shows that less than 0.01% of the power emitted by one antenna is actually going into the other one. This exemplifies the extremely valuable efficiency and predictability benefits obtained by the use of this invention.

Figure 11:
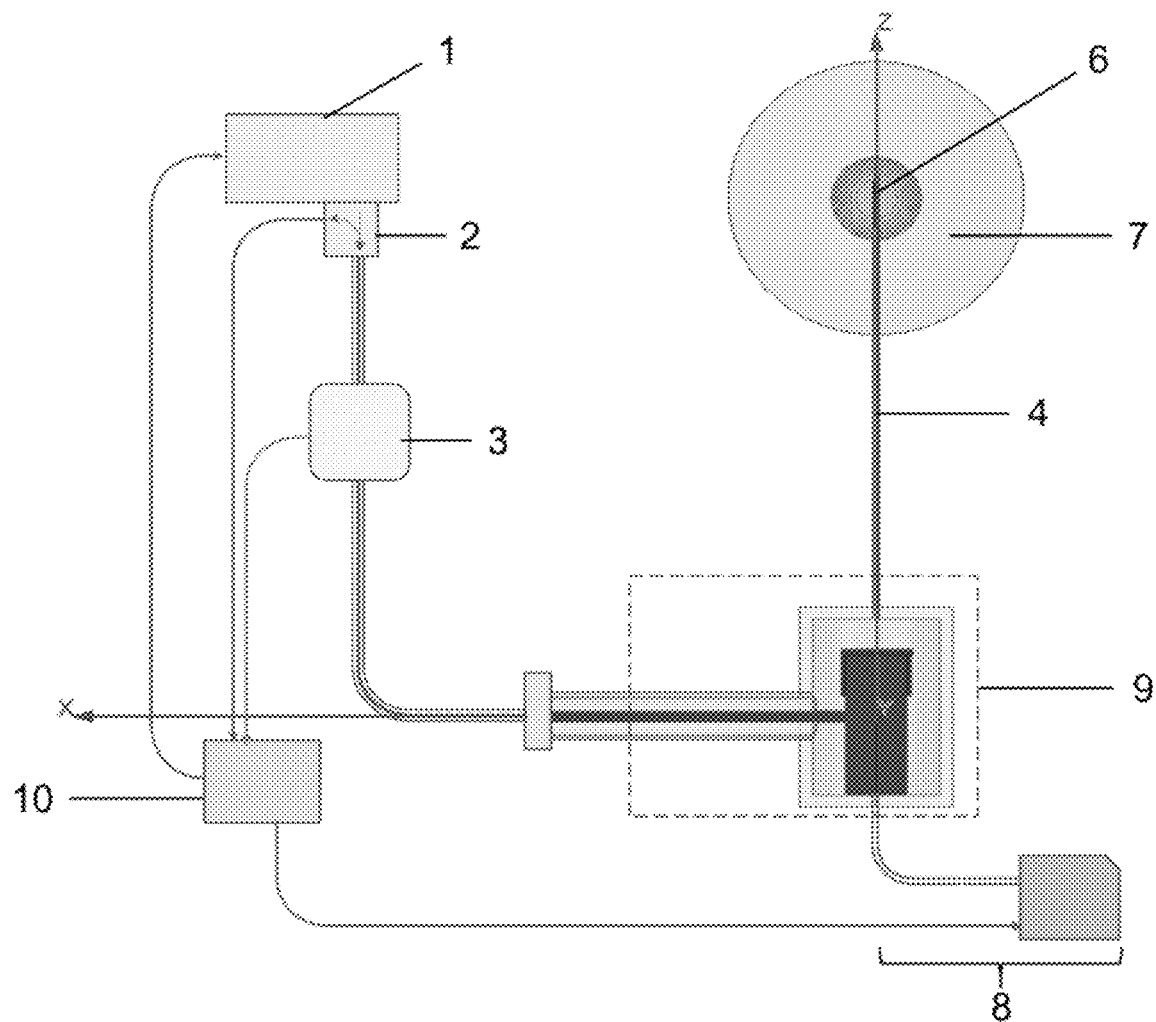
FIG. 11 illustrates a non-limiting example of an apparatus of the present invention, in Use.
Figure 12:
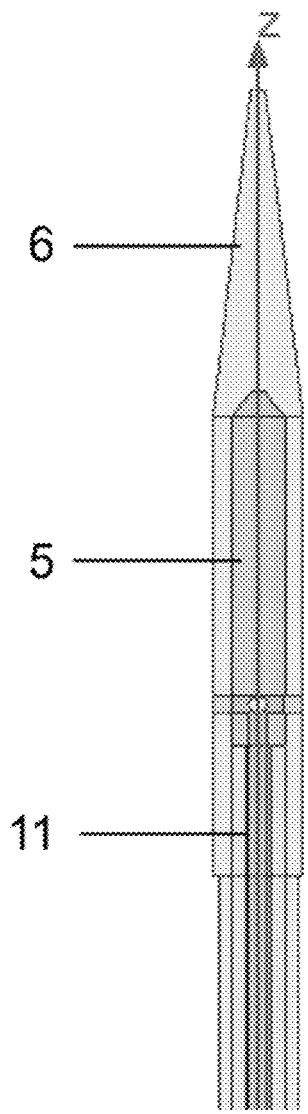
FIG. 12 illustrates a close-up of the probe in FIG. 11.

FIGS. 11 and 12 illustrate an embodiment of the apparatus of the present invention. The apparatus includes a microwave energy generator 1, means to control and measure power and wave characteristics 2, 3 and a needle-like probe 4 connected to the microwave energy generator 1 to transmit and control the microwave energy into affected tissues 7. The needle-like probe 4 includes a microwave antenna 5 and a conduit 11 in a very center thereof. The needle-like probe 4 may have a fritted tip 6. Susceptor is provided for continuous delivery into affected tissues through the conduit 11 simultaneously to the transmission of microwave energy. A control means 8 is provided to control delivery of the susceptor. Further monitor and control means 9 is provided to monitor and control impedance and injection of susceptor into the central conduit 11 of the needle-like probe 4. A further control means 10 is provided to monitor and control the apparatus components.

The quasi-perfect spherical heating pattern is obtained when using a preferred embodiment of this invention, namely that of the unique combination of introducing the ethanol via the same device that is used to transmit the microwave energy. In its most preferred form the method introduces the ethanol continuously as the microwaves are being transmitted to the tissues. This allows maintaining the overall dielectric properties of the tissues more constant than when performing an ablation without such addition of ethanol. One skilled in the art will recognise that the continuous addition of some ethanol provides a means to effect a slower and more progressive reduction in permittivity than that occurring when no ethanol is used or when ethanol is introduced only prior to transmitting the microwave energy. Under current microwave ablation procedures, water is quickly lost as it reaches high temperatures and the permittivity of the tissues near the end of the means to transmit the microwave energy decreases rapidly, thus leading to rapid changes in the electric field pattern, the latter being a most important parameter in the heating and ablative capacity of the procedure. The teachings of this invention are not plagued by such abrupt changes and produces ablation patterns more spherical and more predictable than other microwave ablation procedures currently used.

In the above narrative the word ablation was used for conciseness and one skilled in the art will understand that it does not limit the applicability of the method to other treatments such as thermal coagulation necrosis, atrial fibrillation, resection, cautery, vascular thrombosis, treatment of cardiac arrhythmias and dysrhythmias, electro-surgery, tissue harvest, hemorrhoids thermal coagulation, and other types of thermal alterations. This list itself is also provided only as a list of typical examples and is not exhaustive nor is it limitative with respect to the extent of the applicability and the scope of this invention.

It will be evident that changes can be made to the teachings of the present invention which are disclosed throughout the disclosure herein and by way of changes which Applicant contemplates. For example, in medical applications where drug delivery is contemplated, the drug can be heated prior to delivery and separately from tissues (i.e., two antennas); further another alternative contemplated by the present invention is the fact that the temperature of tissues can be up to and above necrosis if removal or destruction is the target. Alternatively, the temperature of tissues can be kept below necrosis if the target of the invention is a cure. This method is performed to make use of the benefits of the accelerated kinetics of a chemical reaction with increasing temperature as governed by the so-called Arrhenius equation.

It will be evident that other changes can be made to the teachings of the present invention which are disclosed throughout the disclosure herein and by way of changes which Applicant contemplates. For example, in chemical transformations cases where the delivery of reagents is concerned the reagents can be heated prior to delivery and separately from the medium (i.e., two antennas). This method is also performed to make use of the benefits of the accelerated kinetics of a chemical reaction with increasing temperature as governed by the so-called Arrhenius equation.

Further, it will also be evident to those skilled in the art that for all these teachings, a plurality of sources of microwave energy can be used. This may be desirable and can bring additional benefits in medical applications for drug efficiency enhancements for example, but not limited to those. This may be desirable and can bring additional benefits in chemical applications such as solid-phase synthesis for example, or syntheses carried out in media with high dielectric constant that hinders the transmission of the waves, but not limited to those. This is especially desirable in the plasma generation applications where the use of a plurality of microwave sources is already common. Combining this plurality of sources to the introduction of a gas at each microwave-emitted point within a plasma cavity is a most preferred embodiment of this invention.

The use of the words "source of microwave energy" does not limit the method to using a single such microwave generating means, nor does it limit the apparatus to be comprised of a single microwave generator. It is not intended to limit the quantity, nor the type of generators used, nor the frequency at which they operate, the latter can be chosen according to the dielectric properties of the tissues to be treated. It will be known to those skilled in the art that the practice of these teachings lend themselves particularly well to the use of modern variable frequency low-power solid-state generators, but does not preclude the use of any other means to generate microwave energy.

Additionally, it will also be evident to those skilled in the art that for all these teachings, the energy delivering device or plurality of devices can be used and controlled independently and in real time to adapt to the evolving dielectric nature of the materials under treatment. For example, when a plurality of sources are used, each source can be used to measure the properties of the materials under treatment at the specific location where the energy delivery device is inserted and can react accordingly so as to maintain so-called adapted impedance conditions thus maximising the efficiency of the energy delivery process and reducing the delivery of energy to non-targeted areas. Further, one skilled in the art will understand that a most preferred approach to create and control these adapted impedance conditions, lies in the use of modern variable frequency low-power solid-state generators and generators capable to control the phase of the microwave energy being transmitted to the system to be treated but does not preclude the use of any other means to generate microwave energy.

In another example, the energy delivery device such as the antennas, can be moved physically independently one from another in order to be located into areas where the impedance is relatively constant compared to the initial treatment conditions. This is achieved relatively easily by simply deploying an array of antennas at different length and over varying conditions of time according to the evolving dielectric characteristics of the materials under treatment.

In a further example, the energy delivery device such as the antennas, can be moved physically independently one from another in order to be located into areas where the impedance is relatively constant compared to the initial treatment conditions as per above. This is combined with the use of a plurality of variable frequency microwave generators that are operated and controlled independently so as to be able to adapt to the prevailing dielectric conditions wherever the microwave energy is being transmitted, such control includes frequency, power, phase, and time.

Thus the teachings of this invention provide methods that offer the following inventive steps and utilities over existing ones:

they apply to all types of materials;
they require less power;
they require less time;
they enhance the temperature gradient;
they reduce the potential of collateral damage due to non-selective heating and thermal diffusion (such as damages to healthy tissues or side chemical reactions);
they enhance the efficiency of chemical reactions (such as the efficiency of drugs, allowing to use lesser quantities thus reducing side effects and potential addiction issues);
they do not necessarily require an ancillary means of cooling; and
in medical applications they cause less physiological stress to the patient (due to reduced exposure time and basically no harm to healthy tissues).

One skilled in the art will understand that this invention is not limited as to the selection of the guidance technique to be used in conjunction with it and ultrasound guidance can be used as readily as magnetic resonance guidance, the latter being in closed or open form.

In the above narrative the example used deals with the delivery of a liquid substance—ethanol for example—used to modify the dielectric properties of the materials to be treated. This example was used for conciseness and one skilled in the art will understand that it does not limit the applicability of the method to other processes and the introduction and delivery of other substances including but not limited to liquids and gases such as in the generation of plasma under microwave irradiation and other types of microwave-assisted processes such as chemical synthesis. This list itself is also provided only as a list of typical examples and is not exhaustive nor is it limitative with respect to the extent of the applicability and the scope of this invention.

One skilled in the art will recognise that plasmas are generated by supplying energy to a gas or a combination of gases causing the formation of charge carriers. Electrons and ions are produced in the gas phase when electrons or photons with sufficient energy collide with the neutral atoms and molecules in the feed gas (electron-impact ionization or photoionization). For example, while there are various ways to supply the necessary energy for plasma generation to a neutral gas, the most commonly used method of generating and sustaining a low-temperature plasma for technological and technical application is by applying an electric field to a neutral gas. This method utilizes the electrical breakdown of a neutral gas in the presence of an external electric field. The spatial and temporal characteristics of a plasma depend to a large degree on the particular application for which the plasma will be used.

Those skilled in the art know that discharges excited and sustained by high-frequency electromagnetic fields such as radiofrequency (RF) and microwaves are of increasing interest for technical and industrial applications. The power absorption per unit volume by a plasma in a high-frequency field is governed by the electron density, the electron charge, the electron mass, the electron-neutral collision frequency and the angular frequency of the electromagnetic field of a given amplitude. In the presence of a magnetic field B perpendicular to the electric field, an additional parameter becomes of importance, namely the electron cyclotron frequency. Electromagnetic waves with frequencies below the electron plasma frequency will be reflected. The electron density corresponding to the electron plasma frequency is called the cut-off density. However, the so-called skin effect enables the penetration of the wave into the plasma to some extent. The power absorption is limited to the dimension of the skin sheath and its thickness.

A typical non-thermal plasma with an electron density of $10^{10}$ cm$^{-3}$ and an electron-neutral collision frequency of $10^9$ s$^{-1}$ has a skin depth of 0.25 m and 0.02 m, respectively, for frequencies of 13.56 MHz and 2.45 GHz.

RF discharges usually operate in the frequency range 1-100 MHz. The corresponding wavelengths (ca. 3-300 m) are large compared to the dimensions of the plasma reactor. For microwaves the most commonly used frequency is 2.45 GHz corresponding to a wavelength of ca. 12.24 cm. This wavelength is roughly comparable to the dimensions of a typical microwave reactor. For lower frequencies, the ions accelerated in the field move towards the electrodes and produce secondary electrons, similar to what happens in a dc discharge. As the frequency increases, the ions and subsequently also the electrons can no longer reach the electrode surface during the acceleration phase of the exciting external field.

As it will be evident to those skilled in the art, the use of this invention to judiciously locate multiple antennas use to introduce multiple sources of gas to be ionized while applying controlled microwave energy will provide means to enlarge the surface area with controllable plasma generation. It will also be evident to one skilled in the art that this can be combined with the use of a plurality of microwave generators that are operated and controlled independently one from another so as to be able to adapt to the prevailing dielectric conditions wherever the microwave energy is being transmitted. In the most preferred aspect of this invention these plurality of microwave generators are capable of controlling frequency, power, phase, and time.

One skilled in the art will recognise that injecting gas that absorbs microwaves through the microwave transmission means effectively makes the antenna the actual plasma source and the gas becomes absorbing only when it reaches the plasma phase. This offers the advantage of injecting the gas directly in the plasma generation zone. In a preferred embodiment of this invention high-value added molecular gases will be used to further optimise the dissociation of such gases during the process. It can also serve to optimise the dissociation of the gas for high value-added processes such as diamond deposition.

It will be evident to one skilled in the art that this invention applies equally well to other types of procedures performed under plasma and that the above applications are provided herein only as typical examples and that they do not constitute an exhaustive list of applications nor are they limitative with respect to the extent of the applicability and the scope of this invention.

In particular one skilled in the art will recognise the applicability of the invention in various areas such as surface modification (such as etching, structuring, cleaning), functionalization (such as hydrophilization, hydrophobization, graftability, adhesability, printability), interstitial modification (such as diffusion, implantation), deposition (such as change of mechanical, chemical, electrical and optical properties), architecturing (such as crystallographics and morphologic), volume-related transformation (such as energy conversion, high-pressure metal vapour lamps gas lasers, excimer radiation sources, fusion, plasma chemistry (such as transforming into specific compounds, production of precursors, production of excimers, clean-up of gases, odours, flue gases, and diesel exhaust).

In another preferred aspect of the present invention, there is provided apparatus for the enhancement of the efficiency of a drug acting as a susceptor which comprises the following components:
a) a microwave energy source generator;
b) a means to transmit said microwave energy into the affected tissues;
c) a means to deliver a drug into said affected tissues while the temperature of said tissues is higher than normal and higher than surrounding tissues; and optionally
d) a means to control the repetition of steps a) to c) multiple times until the drug delivery is complete, the location of said drug delivery in steps a) to c) being varied between each sequence.

In another preferred aspect of the present invention, there is provided apparatus for the enhancement of the efficiency of a drug acting as a susceptor which comprises the following components:
a) a microwave energy source generator;
b) a means to transmit said microwave energy into the affected external or surface tissues;
c) a means to remove electric field losses to the surrounding non-tissues environment;
d) a means to deliver a drug into said affected external or surface tissues while the temperature of said tissues is higher than normal and higher than surrounding tissues; and optionally
e) a means to control the repetition of steps a) to c) multiple times until the drug delivery is complete, the location of said drug delivery in steps a) to c) being varied between each sequence.

In another preferred aspect of the present invention, there is provided an apparatus for the enhancement of the efficiency of a drug acting as a susceptor which comprises the following components:
a) a microwave energy source generator;
b) a means to transmit said microwave energy into said affected tissues;
c) a means to concentrate the electric field component of said microwave energy into said affected tissues so as to increase selectively the temperature of said affected tissues;
d) a means to deliver a drug into said affected tissues while the temperature of said tissues is higher than normal and higher than surrounding tissues; and optionally
e) a means to control the repetition of steps a) to d) multiple times until the drug delivery is complete, the location of said drug delivery in steps a) to d) being varied between each sequence.

In another preferred aspect of the present invention, there is provided an apparatus for the enhancement of the efficiency of a drug acting as a susceptor which comprises the following components:
a) a microwave energy source generator;
b) a means to transmit said microwave energy into said affected external or surface tissues;
c) a means to concentrate the electric field component of said microwave energy into said affected tissues so as to increase selectively the temperature of said affected tissues;
d) a means to remove electric field losses to the surrounding non-tissues environment;
e) a means to deliver a drug into said affected tissues while the temperature of said tissues is higher than normal and higher than surrounding tissues; and optionally
f) a means to control the repetition of steps a) to d) multiple times until the drug delivery is complete, the location of said drug delivery in steps a) to d) being varied between each sequence.

In yet a further preferred aspect of the present invention, there is provided an apparatus for the enhancement of the efficiency of a drug acting as a susceptor which comprises the following components:
a) a microwave energy source generator;
b) a means to transmit said microwave energy into a drug used to treat affected tissues;
c) a means to deliver said drug into said affected tissues while the temperature of said drug is higher than room temperature and higher than surrounding tissues, but below a temperature that could cause harm to said affected tissues; and optionally
d) a means to control the repetition of steps a) to c) multiple times until the drug delivery is complete, the location of said drug delivery in steps a) to c) being varied between each sequence.

In another preferred aspect of the present invention, there is provided apparatus for the enhancement of the efficiency of a drug acting as a susceptor which comprises the following components:
a) a microwave energy source generator;
b) a means to transmit said microwave energy into a drug used to treat affected tissues;
c) a means to remove electric field losses to the surrounding non-tissues environment;
d) a means to deliver said drug into said affected tissues while the temperature of said drug is higher than room temperature and higher than surrounding tissues, but below a temperature that could cause harm to said affected tissues; and optionally
e) a means to control the repetition of steps a) to d) multiple times until the drug delivery is complete, the location of said drug delivery in steps a) to d) being varied between each sequence.

In yet a further preferred aspect of the present invention, there is provided an apparatus for the enhancement of the efficiency of a drug acting as a susceptor which comprises the following components:
a) a microwave energy source generator;
b) a means to transmit said microwave energy into a drug acting as a susceptor used to treat affected tissues;
c) a means to concentrate the electric field component of said microwave energy into the drug used to treat affected tissues so as to increase selectively the temperature of said drug;
d) a means to deliver said drug into said affected tissues while the temperature of said drug is higher than room temperature and higher than surrounding tissues, but below a temperature that could cause harm to said affected tissues; and optionally
e) a means to control the repetition of steps a) to d) multiple times until the drug delivery is complete, the location of said drug delivery in steps a) to d) being varied between each sequence.

In yet a further preferred aspect of the present invention, there is provided an apparatus for the enhancement of the efficiency of a drug acting as a susceptor which comprises the following components:
- a) a microwave energy source generator;
- b) a means to transmit said microwave energy into a drug used to treat affected tissues;
- c) a means to concentrate the electric field component of said microwave energy into the drug used to treat affected tissues so as to increase selectively the temperature of said drug;
- d) a means to remove electric field losses to the surrounding non-tissues environment;
- e) a means to deliver said drug into said affected tissues while the temperature of said drug is higher than room temperature and higher than surrounding tissues, but below a temperature that could cause harm to said affected tissues; and optionally
- f) a means to control the repetition of steps a) to e) multiple times until the drug delivery is complete, the location of said drug delivery in steps a) to e) being varied between each sequence.

In a still further preferred aspect of the present invention, there is provided an apparatus for the enhancement of the efficiency of a drug acting as a susceptor which comprises the steps of:
- a) a microwave energy source generator;
- b) a means to transmit said microwave energy into a drug used to treat the affected tissues and into said affected tissues;
- c) a means to deliver said drug into said affected tissues while the temperature of said drug and said affected tissues is higher than surrounding tissues but below a temperature that could cause harm to said affected tissues; and optionally
- d) a means to control the repetition of steps a) to c) multiple times until the drug delivery is complete, the location of said drug delivery in steps a) to c) being varied between each sequence.

In a still further preferred aspect of the present invention, there is provided an apparatus for the enhancement of the efficiency of a drug acting as a susceptor which comprises:
- a) a microwave energy source generator;
- b) a means to transmit said microwave energy into a drug used to treat the affected tissues and into said affected tissues;
- c) a means to remove electric field losses to the surrounding non-tissues environment;
- d) a means to deliver said drug into said affected tissues while the temperature of said drug and said affected tissues is higher than surrounding tissues but below a temperature that could cause harm to said affected tissues; and optionally
- e) a means to control the repetition of steps a) to d) multiple times until the drug delivery is complete, the location of said drug delivery in steps a) to d) being varied between each sequence.

In a still further preferred aspect of the present invention, there is provided an apparatus for the enhancement of the efficiency of a drug acting as a susceptor which comprises the steps of:
- a) a microwave energy source generator;
- b) a means to transmit said microwave energy into a drug used to treat the affected tissues and into said affected tissues;
- c) a means to concentrate the electric field component of said microwave energy into the drug used to treat affected tissues so as to increase selectively the temperature of said drug;
- d) a means to deliver said drug into said affected tissues while the temperature of said drug and said affected tissues is higher than surrounding tissues but below a temperature that could cause harm to said affected tissues; and optionally
- e) a means to control the repetition of steps a) to c) multiple times until the drug delivery is complete, the location of said drug delivery in steps a) to c) being varied between each sequence.

In a still further preferred aspect of the present invention, there is provided an apparatus for the enhancement of the efficiency of a drug acting as a susceptor which comprises the steps of:
- a) a microwave energy source generator;
- b) a means to transmit said microwave energy into a drug used to treat the affected tissues and into said affected tissues;
- c) a means to concentrate the electric field component of said microwave energy into the drug used to treat affected tissues so as to increase selectively the temperature of said drug;
- d) a means to remove electric field losses to the surrounding non-tissues environment;
- e) a means to deliver said drug into said affected tissues while the temperature of said drug and said affected tissues is higher than surrounding tissues but below a temperature that could cause harm to said affected tissues; and optionally
- f) a means to control the repetition of steps a) to e) multiple times until the drug delivery is complete, the location of said drug delivery in steps a) to e) being varied between each sequence.

In a still preferred aspect of the present invention, there is provided an apparatus for the enhancement of the efficiency of a chemical ablation procedure which comprises the steps of:
- a) a microwave energy source generator;
- b) a means to transmit and control said microwave energy into affected tissues;
- c) a means to deliver a chemical agent acting as a susceptor used for the chemical ablation into said affected tissues simultaneously to said transmission of said microwave energy into said affected tissues;
- d) a means to monitor in real-time the electric field resulting from said simultaneous transmission of said microwave energy and said delivery of said chemical agent used for said chemical ablation into said affected tissues;
- e) a means to monitor and control in real-time the delivery and quantity of said chemical agent being used for said chemical ablation into said affected tissues;
- f) a means to monitor and control in real-time the temperature raising from said simultaneous transmission of said microwave energy and said controlled delivery of said chemical agent used for said chemical ablation into said affected tissues so as to maintain the temperature of said affected tissues and said chemical agent used for said chemical ablation into said affected tissues higher than surrounding tissues;
- g) a means to respond and control in real-time the simultaneous exposure of said affected tissues to said electric field and said chemical agent used for said chemical ablation and said increased temperature to thereby ablate, remove, coagulate or otherwise alter said affected tissues; and optionally h) a means to control the repetition of steps a) to g) multiple times until the chemical ablation agent delivery is complete, the location of said chemical ablation agent delivery in steps a) to g) being varied between each sequence.

In a most preferred aspect of the present invention, there is provided an apparatus for the enhancement of the efficiency of a chemical ablation procedure which comprises the steps of:

a) a microwave energy source generator;

b) a means to transmit and control said microwave energy into affected tissues;

c) a means to deliver a chemical agent acting as a susceptor used for a chemical ablation into said affected tissues simultaneously to said transmission of said microwave energy into said affected tissues, said delivery of said chemical agent used for the chemical ablation being effected through said microwave transmitting means;

d) a means to monitor in real-time the electric field resulting from said simultaneous transmission of said microwave energy and said delivery of said chemical agent used for said chemical ablation into said affected tissues;

e) a means to monitor and control in real-time the delivery and quantity of said chemical agent being used for said chemical ablation into said affected tissues;

f) a means to monitor and control in real-time the temperature raising from said simultaneous transmission of said microwave energy and said controlled delivery of said chemical agent used for said chemical ablation into said affected tissues so as to maintain the temperature of said affected tissues and said chemical agent used for said chemical ablation into said affected tissues higher than surrounding tissues;

g) a means to respond and control in real-time the simultaneous exposure of said affected tissues to said electric field and said chemical agent used for said chemical ablation and said increased temperature to thereby ablate, remove, coagulate or otherwise alter said affected tissues; and optionally h) a means to control the repetition of steps a) to g) multiple times until the chemical ablation agent delivery is complete, the location of said chemical ablation agent delivery in steps a) to g) being varied between each sequence.

In a still preferred aspect of the present invention, there is provided an apparatus for the enhancement of the efficiency and the acceleration of the kinetics of a chemical reaction procedure which comprises the steps of:

a) a microwave energy source generator;

b) a means to transmit and control said microwave energy into a chemical reaction medium consisting of at least one chemical reagent neat or in presence of a suitable solvent;

c) a means to deliver at least one other chemical reagent into said chemical reaction medium simultaneously to said transmission of said microwave energy into said chemical reaction medium, said delivery of said chemical reagent used for the chemical reaction being effected through said microwave transmitting means;

d) a means to monitor in real-time the electric field resulting from said simultaneous transmission of said microwave energy and said delivery of said chemical reagent into said chemical reaction medium;

e) a means to monitor and control in real-time the delivery and quantity of said chemical reagent being used for said chemical reaction into said chemical reaction medium;

f) a means to monitor and control in real-time the temperature raising from said simultaneous transmission of said microwave energy and said controlled delivery of said chemical reagent used for said chemical reaction into said chemical reaction medium so as to maintain the temperature of said chemical reaction medium sufficient to effect the chemical reaction;

g) a means to respond and control in real-time the simultaneous exposure of said chemical reaction medium to said electric field and said chemical reagent used for said chemical reaction and said increased temperature to thereby complete the said chemical reaction; and optionally h) a means to control the repetition of steps a) to g) multiple times until the chemical reagent delivery is complete, the location of said chemical reagent delivery in steps a) to g) being varied between each sequence.

In a most preferred aspect of the present invention, there is provided an apparatus for the enhancement of the efficiency and the acceleration of the kinetics of a chemical reaction procedure which comprises the steps of:

a) a microwave energy source generator;

b) a means to transmit and control said microwave energy into a chemical reaction medium consisting of at least one chemical reagent neat or in presence of a suitable solvent;

c) a means to deliver at least one other chemical reagent through the very centre of said energy transmitting and controlling means into said chemical reaction medium simultaneously to said transmission of said microwave energy into said chemical reaction medium;

d) a means to monitor in real-time the electric field resulting from said simultaneous transmission of said microwave energy and said delivery of said chemical reagent into said chemical reaction medium;

e) a means to monitor and control in real-time the delivery and quantity of said chemical reagent being used for said chemical reaction into said chemical reaction medium;

f) a means to monitor and control in real-time the temperature raising from said simultaneous transmission of said microwave energy and said controlled delivery of said chemical reagent used for said chemical reaction into said chemical reaction medium so as to maintain the temperature of said chemical reaction medium sufficient to effect the chemical reaction;

g) a means to respond and control in real-time the simultaneous exposure of said chemical reaction medium to said electric field and said chemical reagent used for said chemical reaction and said increased temperature to thereby complete the said chemical reaction; and optionally h) a means to control the repetition of steps a) to g) multiple times until the chemical reagent delivery is complete, the location of said chemical reagent delivery in steps a) to g) being varied between each sequence.

One skilled in the art will also recognise that for the previous aspects of the invention the terms "solvent" and "solubilised" were chosen as examples for conciseness and that they can be substituted for "support" and "dispersed" as this invention also contemplates the performance of a solid-phase chemical reaction and is not limited to liquid-state reactions. One skilled in the art will appreciate that step "h" of the previous two aspects of this invention contemplates preferably such solid-phase synthesis.

In a still preferred aspect of the present invention, there is provided an apparatus for the generation of plasma comprising the steps of:

a) a microwave energy source generator;

b) a means to transmit and control said microwave energy into a reaction chamber;

c) a means to deliver at least one gaseous material into said reaction chamber simultaneously to said microwave energy transmission into said reaction chamber, said delivery of said gaseous material being effected through said microwave transmitting means;

d) a means to monitor in real-time the electric field resulting from said simultaneous transmission of said microwave energy and said delivery of said gaseous material into said reaction chamber;

e) a means to monitor and control in real-time the delivery and quantity of said gaseous material into said chemical reaction chamber;

f) a means to monitor and control in real-time the dielectric properties in said reaction chamber caused by said simultaneous transmission of said microwave energy and said controlled delivery of said gaseous material into said reaction chamber so as to maintain conditions capable to generate plasma materials; and g) a means to maintain said exposure of said gaseous materials to said microwave energy under said conditions capable to generate plasma materials until the desired process is complete.

In a most preferred aspect of the present invention, there is provided an apparatus for the generation of plasma comprising the steps of:

a) a microwave energy source generator;

b) a means to transmit and control said microwave energy into a reaction chamber;

c) a means to deliver at least one gaseous material through the very centre of said energy transmitting and controlling means into said reaction chamber simultaneously to said microwave energy transmission into said reaction chamber;

d) a means to monitor in real-time the electric field resulting from said simultaneous transmission of said microwave energy and said delivery of said gaseous material into said reaction chamber;

e) a means to monitor and control in real-time the delivery and quantity of said gaseous material into said chemical reaction chamber;

f) a means to monitor and control in real-time the dielectric properties in said reaction chamber caused by said simultaneous transmission of said microwave energy and said controlled delivery of said gaseous material into said reaction chamber so as to maintain conditions capable to generate plasma materials; and g) a means to maintain said exposure of said gaseous materials to said microwave energy under said conditions capable to generate plasma materials until the desired process is complete.

| References Cited | | |
|---|---|---|
| U.S. Patent Documents | | |
| 5,002,784 | March 1991 | Paré et al. |
| 5,338,557 | August 1994 | Paré |
| 5,458,897 | October 1995 | Paré |
| 5,377,426 | January 1995 | Paré |
| 5,519,947 | May 1996 | Paré |
| 5,675,909 | October 1997 | Paré |
| 5,732,476 | March 1998 | Paré |
| 6,061,926 | May 2000 | Paré et al. |
| 8,343,095 | January 2013 | Cressman |
| 9,498,284 | November 2016 | McErlean et al. |
| 9,526,557 | December 2016 | Brannan |
| 9,526,568 | December 2016 | Ohri et al. |
| 9,526,576 | December 2016 | Brannan |
| Foreign Patent Documents | | |
| 3,095,241 | (2000) | JP |

OTHER REFERENCES

J. M. R. Bélanger et al., "Influence of Solvent, Matrix Dielectric Properties, and Applied Power on the Liquid-Phase Microwave-Assisted Process (MAP™) Extraction of Ginger (*Zingiber Officinale*)", Food Research International, 2003; 36, 499-504.

Bélanger et al., "Microwave-Assisted Processes (MAP™) in Food Analysis", in Otles S (ed.): *Handbook of Food Analysis Instruments*, CRC Press, Chapter 4, (2008), pp. 57-83.

Bélanger et al., "Survey of Recent Industrial Applications of Microwave Energy Applications", Journal of Microwave Power and Electromagnetic Energy, 2008; 42 (4), 24-44.

Du et al. "Gelatin Microcapsules for Enhanced Microwave Tumor Hyperthermia", Nanoscale 2015; 7, 31473154.

Dou et al., "Microwave Ablation for Liver Tumors", Abdominal Radiology, 2016; 41, 650-658.

Goldberg et al., "Radio-Frequency Thermal Ablation with NaCl Solution Injection: Effect of Electrical Conductivity on Tissue Heating and Coagulation—Phantom and Porcine Liver Study," Radiology, 2001; 219:157-165.

Liu et al., "Optimization of Microwave Applicator for Improved Energy Efficiency and Homogeneity", *Chemistry Today* 29 (4), 14-17 (2011).

Mutyala et al., "Microwave Applications to Oil Sands and Petroleum: A Review", Fuel Processing Technology, 2010; 91(2), 127-135.

Mutyala et al., "Design and Numerical Simulation of High-efficiency Microwave Applicator for Industrial Processes", Hydrocarbon World, 2011; 6, 271-275.

Paré et al., "Microwave-Assisted Process (MAP™): a New Tool for the Analytical Laboratory", Trends in Analytical Chemistry 1994; 13, 176-184.

Paré et al., "Microwave-Assisted Process (MAP™): Principles and Applications" In Paré J R J, Bélanger J M R (eds.) Instrumental Methods in Food Analysis", Amsterdam, Elsevier Science, Chapter 10, (1997), pp. 395-420.

Paré et al., "Microwave-Assisted Extraction" In Pawliszyn J, Lord H (eds): Sample Preparation Handbook, John Wiley & Sons (USA), Chapter 12, (2010), pp. 197-224.

Shi et al. "Insights into a Microwave Susceptible Agent for Minimally Invasive Microwave Tumor Thermal Therapy", Biomaterials, 2015; 44, 91-102.

The invention claimed is:

1. An apparatus for the enhancement of the efficiency of an ablation procedure which comprises:
   a) a microwave energy source generator;
   b) a needle-like probe for connection to the microwave energy source generator to transmit and control said microwave energy into affected tissues, said needle-like probe having a microwave antenna and a conduit in a very center thereof;
   c) a susceptor for continuous delivery into affected tissues through the conduit and simultaneously to said transmission of said microwave energy into said affected tissues, wherein said susceptor is characterized by dielectric properties, permittivity and loss factor, allowing to continuously control evolution of dielectric properties of said affected tissue under treatment, the susceptor reducing dielectric changes brought about by water displaced from the affected tissue as a result of treatment, said susceptor continuously controlling dielectric properties and impedance conditions of said affected tissues;
   d) means to monitor in real-time an electric field resulting from said simultaneous transmission of said microwave energy and said delivery of said susceptor into said affected tissues;
   e) control means for controlling delivery of the susceptor to continuously control in real-time evolution of dielectric properties of the affected tissue under treatment as the electric field moves away from a microwave emitting point so as to maintain electrical conditions where an impedance at the microwave emitting point and a delivery point of said susceptor remains constant, by controlling the delivery of the susceptor simultaneously with the delivery of the microwave energy;
   f) monitor and control means for monitoring and controlling in real-time the simultaneous exposure of said affected tissues to said electric field. and said susceptor and a temperature to thereby ablate, remove, coagulate or otherwise alter said affected tissues; and
   g) a controller to control the repetition of steps a) to multiple times until the susceptor delivery is complete, the location of said susceptor delivery in steps a) to f) being varied between each sequence.

2. The apparatus according to claim 1 wherein the needle-like probe has a dielectric fritted eluting tip.

3. The apparatus according to claim 1 wherein said antenna can he retracted and introduced in a different location of said affected tissue.

4. The apparatus according to claim 1 wherein affected tissues are heated to and above necrosis temperature if removal or destruction is intended.

5. The apparatus according to claim 1 wherein the temperature of tissues is kept below necrosis temperature if a cure is intended.

6. The apparatus according to claim 1 wherein said susceptor is ethanol.

* * * * *

UNITED STATES PATENT AND TRADEMARK OFFICE
CERTIFICATE OF CORRECTION

| | |
|---|---|
| PATENT NO. | : 11,589,922 B2 |
| APPLICATION NO. | : 17/372063 |
| DATED | : February 28, 2023 |
| INVENTOR(S) | : J. R. Jocelyn Paré et al. |

It is certified that error appears in the above-identified patent and that said Letters Patent is hereby corrected as shown below:

In the Claims

In Column 38, Line 8, Claim 1, delete "field." and insert -- field --, therefor.

In Column 38, Line 11, Claim 1, delete "a) to" and insert -- a) to f) --, therefor.

In Column 38, Line 18, Claim 3, delete "can he" and insert -- can be --, therefor.

Signed and Sealed this
Seventh Day of November, 2023

Katherine Kelly Vidal
*Director of the United States Patent and Trademark Office*